United States Patent
Lock et al.

(10) Patent No.: US 11,644,899 B2
(45) Date of Patent: May 9, 2023

(54) BIOMETRIC ENABLED VIRTUAL REALITY SYSTEMS AND METHODS FOR DETECTING USER INTENTIONS AND MODULATING VIRTUAL AVATAR CONTROL BASED ON THE USER INTENTIONS FOR CREATION OF VIRTUAL AVATARS OR OBJECTS IN HOLOGRAPHIC SPACE, TWO-DIMENSIONAL (2D) VIRTUAL SPACE, OR THREE-DIMENSIONAL (3D) VIRTUAL SPACE

(71) Applicant: COAPT LLC, Chicago, IL (US)

(72) Inventors: Blair Andrew Lock, Chicago, IL (US); Levi John Hargrove, Chicago, IL (US)

(73) Assignee: COAPT LLC, Chicago, IL (US)

( * ) Notice: Subject to any disclaimer, the term of this patent is extended or adjusted under 35 U.S.C. 154(b) by 141 days.

(21) Appl. No.: 17/237,337

(22) Filed: Apr. 22, 2021

(65) Prior Publication Data

US 2022/0342482 A1 Oct. 27, 2022

(51) Int. Cl.
*G06F 3/01* (2006.01)
*G06T 13/40* (2011.01)
(Continued)

(52) U.S. Cl.
CPC ............. *G06F 3/015* (2013.01); *G06T 13/40* (2013.01); *G06T 13/80* (2013.01); *G06T 19/20* (2013.01);
(Continued)

(58) Field of Classification Search
CPC ................. G06T 2200/24; G06T 19/20; G06T 2219/2012; G06T 2219/2016; G06T 13/80; G06T 13/40; G06F 3/0482; G06F 3/015
See application file for complete search history.

(56) References Cited

U.S. PATENT DOCUMENTS 9,058,698 B2   6/2015  Jones et al.
9,198,622 B2   12/2015 Kaleal, III et al.
(Continued)

OTHER PUBLICATIONS

Bourdin et al., "Altered visual feedback from an embodied avatar unconsciously influences movement amplitude and muscle activity," Scientific Reports, 9(1):19747 (2019).
Chau et al., "Immersive Virtual Reality Therapy with Myoelectric Control for Treatment-resistant Phantom Limb Pain: Case Report," Innovations in Clincal Neuroscience, 14(7-8):3-7 (2017).
(Continued)

*Primary Examiner* — Muhammad N Edun
(74) *Attorney, Agent, or Firm* — Marshall, Gerstein & Borun LLP

(57) ABSTRACT

Biometric enabled virtual reality (VR) systems and methods are disclosed for detecting user intention(s) and modulating virtual avatar control based on the user intention(s) for creation of virtual avatar(s) or object(s) in holographic space, two-dimensional (2D) virtual space, or three-dimensional (3D) virtual space. A virtual representation of an intended motion of a user corresponding to an intention of muscle activation of the user is determined based on analysis of a biometric signal data of the user as collected by a biometric detection device. The virtual representation of the intended motion is used to modulate virtual avatar control or output to create at least one of a virtual avatar representing aspect(s) of the user or an object manipulated by the user in a holographic space, virtual 2D space, or virtual 3D space. The avatar or the object is created based on: (1) the biometric signal data of a user, or (2) user-specific specifications as provided by the user.

29 Claims, 8 Drawing Sheets

(51) Int. Cl.
G06T 13/80 (2011.01)
G06T 19/20 (2011.01)
G06F 3/0482 (2013.01)

(52) U.S. Cl.
CPC ........ G06F 3/0482 (2013.01); G06T 2200/24 (2013.01); G06T 2219/2012 (2013.01); G06T 2219/2016 (2013.01)

(56) References Cited

U.S. PATENT DOCUMENTS

| | | | |
|---|---|---|---|
| 9,211,077 | B2 | 12/2015 | Jung et al. |
| 9,539,500 | B2 | 1/2017 | Leyvand et al. |
| 9,818,024 | B2 | 11/2017 | Bacivarov et al. |
| 9,883,838 | B2 | 2/2018 | Kaleal, III et al. |
| 10,065,074 | B1 | 9/2018 | Hoang et al. |
| 10,130,298 | B2 | 11/2018 | Mokaya et al. |
| 10,339,365 | B2 | 7/2019 | Gusarov et al. |
| 2015/0356781 | A1 | 12/2015 | Miller |
| 2016/0134840 | A1 | 5/2016 | McCulloch |
| 2016/0364895 | A1 | 12/2016 | Santossio et al. |
| 2017/0326333 | A1* | 11/2017 | Giap ............... A61B 6/037 |
| 2018/0239144 | A1 | 8/2018 | Woods et al. |
| 2019/0384392 | A1 | 12/2019 | Aimone et al. |
| 2020/0234481 | A1 | 7/2020 | Scapel et al. |

OTHER PUBLICATIONS

Consoni et al., "A Robotic Telerehabilitation Game System for Multiplayer Activities," 6th IEEE RAS/EMBS International Conference on Biomedical Robotics and Biomechatronics (BioRob), 806-11 (2016).

Cummins et al., "Machine Learning to Improve Pattern Recognition Control of Upper-Limb Myoelectric Prostheses," Myoelectric Controls and Upper Limb Prosthetic Symposium (2017).

Fernández-Vargas et al., "Effects of Using Virtual Reality and Virtual Avatar on Hand Motion Reconstruction Accuracy and Brain Activity," IEEEAccess, 5:23736-50 (2017).

Hargrove et al., "A Real-Time Pattern Recognition Based Myoelectric Control Usability Study Implemented in a Virtual Environment," 29th Annual International Conference of IEEE-EMBS, Engineering in Medicine and Biology Society (2007).

Kaliki et al., "Evaluation of a Noninvasive Command Scheme for Upper-Limb Prostheses in a Virtual Reality Reach and Grasp Task," IEEE Transactions on Biomedical Engineering, 60(3):792-802 (2013).

Lendaro et al., "Out of the Clinic, into the Home: The in-Home Use of Phantom Motor Execution Aided by Machine Learning and Augmented Reality for the Treatment of Phantom Limb Pain," Journal of Pain Research, 13:195-209 (2020).

Lock et al., "Prosthesis-Guided Training for Practical Use of Pattern Recognition Control of Prostheses," Proceedings of the 2011 MyoElectric Controls/Powered Prosthetics Symposium Fredericton (2011).

Ortiz-Catalan et al., "Treatment of phantom limb pain (PLP) based on augmented reality and gaming controlled by myoelectric pattern recognition: a case study of a chronic PLP patient," Frontiers in Neuroscience, 8(24):1-7 (2014).

Park et al., "Tele-Impedance Control of Virtual System with Visual Feedback to Verify Adaptation of Unstable Dynamics during Reach-to-Point Tasks," 6th IEEE RAS/EMBS International Conference on Biomedical Robotics and Biomechatronics (BioRob), 1283-89 (2016).

Pasqual et al., "Serious Game Development for Ankle Rehabilitation Aiming at User Experience," 6th IEEE RAS/EMBS International Conference on Biomedical Robotics and Biomechatronics (BioRob), 1015-20 (2016).

Perry et al., "Virtual Integration Environment as an Advanced Prosthetic Limb Training Platform," Frontiers in Neurology, 9(785):1-8 (2018).

Rizzo, "Virtual reality and disability: emergence and challenge," Disability and Rehabilitation, 24(11-12):567-69 (2002).

Terlaak et al., "Virtual Training of the Myosignal," PLoS ONE, 10(9):1-14 (2015).

Winslow et al., "Mobile, Game-Based Training for Myoelectric Prosthesis Control," Frontiers in Bioengineering and Biotechnology, 6(94):1-8 (2018).

Woodward et al., "Adapting myoelectric control in real-time using a virtual environment," Journal of NeuroEngineering and Rehabilitation, 16(11):1-12 (2019).

* cited by examiner

BIOMETRIC ENABLED VIRTUAL REALITY SYSTEMS AND METHODS FOR DETECTING USER INTENTIONS AND MODULATING VIRTUAL AVATAR CONTROL BASED ON THE USER INTENTIONS FOR CREATION OF VIRTUAL AVATARS OR OBJECTS IN HOLOGRAPHIC SPACE, TWO-DIMENSIONAL (2D) VIRTUAL SPACE, OR THREE-DIMENSIONAL (3D) VIRTUAL SPACE

FIELD OF THE DISCLOSURE

The present disclosure generally relates to biometric enabled virtual reality (VR) systems and methods, and more particularly to biometric enabled virtual reality systems and methods for detecting one or more user intentions and manipulating virtual avatar control based on the one or more user intentions for providing kinematic awareness in holographic, two-dimensional (2D), or three-dimensional (3D) virtual space. The present disclosure further relates to detecting one or more user intentions, and modulating virtual avatar control based on the one or more user intentions, for creation of one or more virtual avatars in holographic, 2D, or 3D virtual space. The disclosure describes devices configured for, and methods adapted for, collecting biometric signal information from a user and providing a dynamic interpretation of biometric signals through a virtual avatar, as well as generating a virtual representation of kinesthetic awareness and/or a desired appearance of a user in either holographic space or via VR in 2D or 3D virtual space.

BACKGROUND

The utilization of computers to generate virtual avatars and lifelike images are becoming more prevalent. Devices configured for Virtual Reality (VR) applications are becoming increasingly available and are increasing used on a widespread basis. Many of these technologies are beginning to take advantage of projectors, Augmented Reality (AR), and holograms to immerse patrons in these new computer-generated experiences (e.g., a MICROSOFT MESH enabled device, FARYUAN FAN holographic LED projector, etc.). In addition, VR functionality is continuously evolving—resulting in increased setup time and/or proprietary virtual representations. The various, and often different, VR devices typically require reference points, cameras, or other visual technologies used to capture image(s) of a user along with any motions the user is making and/or attempting to make. For example, current techniques for displaying a virtual representation of a user in virtual space, such as through a video conference meeting (e.g., ZOOM, GOOGLE HANGOUTS, etc.), have been developed around camera and Lidar technology, which are configured to record image(s) of a user and to replay the captured image(s) to other members within the virtual space. Such technologies can demonstrate current physical state, including motions, positions, temporal changes in the recorded images, and can replay such images back in virtual space. However, without the use of video (e.g., camera, lidar, etc.) capture, a user of these typical technologies cannot augment his or her personal image or control his or her virtual avatar in virtual space. In addition, current VR technology remains unable, or insufficiently capable, of advanced user analysis, including, for example, determining complex motions, categorizing users based on preferred perceptions, and accurately portraying a motion of a user when a user lacks the physical capacity to perform the motion.

Furthermore, in the event that a user has either an amputated extremity, a bilateral amputation, a physical deformity, or a pathophysiology relating to the neurological or muscular control of extremities, traditional technologies do not have the capacity to provide a user with adequate control, thereby preventing the user from attaining optimal biometric control or proper kinematic awareness. This is especially so in cases wherein a patient has removed or diminished control of an extremity, e.g., via an amputation. In such scenarios, existing techniques for creating a visual reference for the purpose of treating ailments, such as "phantom limb pain" (PLP), have been ineffective. For example, traditional methods of treating PLP involve using a reference technology, such as a mirror or camera, to monitor both an injured and an uninjured extremity. In such traditional treatments, a user is instructed to move an uninjured extremity while simultaneously attempting to activate the muscles of an injured, typically amputated, extremity. The existing technology then recreates the image of how the injured extremity would have appeared to the user, superimposing the image over the amputated extremity as if the amputated extremity had not been amputated. This technique of recreating a visual image of an extremity that otherwise doesn't exist has demonstrated increasingly supported neurological value in reducing the amount of "phantom pain" that a user perceives for an amputated body part. However, the above technique does not apply for a user that (a) has bilateral amputation(s) and that does not have a second, uninjured limb that can be used as a visual reference, or (b) a user who is attempting to activate muscles) to make a specific movement, but does not have the physical capacity to make such movement (e.g., muscles are too weak). Still further, such traditional techniques do not measure or track the amplitude of effort for which a user is intending to make a movement. And further still, these traditional techniques do not accurately represent a user's intention to perform a complex movement, in which one or more muscles are activated to perform a motion involving potentially multiple joints.

Still further, existing technologies that rely on superimposing images on user extremities have continued to rely on cameras and accelerometers to detect the physical location and direction of movement of a user. Because of this, the ability for a user to accurately control his or her own perception-of-self is limited based on the cameras and/or accelerometers inherent limitations (e.g., limited frames, angles, and/or configurations), and, therefore, the user's experience can be greatly diminished.

For the foregoing reasons there is a need for biometric enabled virtual reality systems and methods for detecting one or more user intentions and manipulating virtual avatar control based on the one or more user intentions for providing kinematic awareness in holographic, 2D, or 3D virtual space. In particular, the systems and methods disclosed herein improve upon the prior art through a novel system that can quantify the intention of a user to activate a group of muscles, regardless of whether or not the intended motion (e.g., of a non-existent user limb) actually occurs.

In addition, for the foregoing reasons there is a need for biometric enabled virtual reality systems and methods for detecting one or more user intentions and modulating virtual avatar control based on the one or more user intentions for creation of one or more virtual avatars in holographic, 2D, or 3D virtual space.

SUMMARY

Virtual reality (VR), Augmented Reality (AR), and holographic projections are becoming increasingly relevant in social and medical settings. As described herein, VR refers to at least one of Virtual Reality, Augmented Reality, and Holographic Projections. Furthermore, references to virtual space may include but are not limited to 2-Dimensional virtual images, 3-Dimensional virtual images, or holographic images produced through VR, LED Fans (e.g., Faryuan Hologram Fan), or holographic projectors. The importance of having an easy-to-control and accurate VR systems and methods becomes increasingly important to users as VR technologies become more widespread. The present disclosure describes biometric enabled VR systems and methods that provide enhanced VR capabilities and configurations that provide for virtual representation accuracy and rapid setup and configuration based on user-specific preferences and/or physiological profiles, including where user-specific modulation is supplied for personal or medical needs, and which allows for enhanced control for user specific needs, e.g., medical needs.

The biometric enabled virtual reality systems and methods as described herein provide avatar modulation without the need of a visual reference. That is, the present disclosure differs from traditional VR applications at least because the biometric enabled virtual reality systems and methods of the present disclosure do not rely on cameras and imaging as do traditional VR applications. For example, traditional methods of creating virtual images typically require a camera, lidar, or other imaging capture device(s) to detect current and temporal positioning of a user. Such methodology is typically, however, inaccurate and/or incomplete because existing imaging technology lacks the ability to detect the user's biometric signals and, as a consequence, is ineffective at capturing user-specific differences that, as described herein, enhance VR fidelity with respect to representing a user correctly in a VR space.

In addition, the disclosed biometric enabled virtual reality systems and methods can comprise user-specific configuration(s) and/or physiological profiling that provide accurate avatar creation, representation, and/or control with respect to simple and/or complex user motion intentions, enabling users to experience an enhanced VR simulation of their kinematic awareness (e.g., a kinetic self-awareness or proprioception as experienced by the user) in holographic, virtual 2D, or virtual 3D space.

In addition, the present disclosure describes biometric enabled VR systems that have the capacity to measure the user's intention to activate muscles corresponding to an amputated extremity, regardless of whether or not motion is produced by an intention to activate those muscles, which may be non-existent (e.g., due to amputation).

Still further, the present disclosure further describes biometric enabled VR systems and methods for treating medical conditions, where the biometric enabled virtual reality systems and methods comprise capabilities to adapt to a user's unique condition, and by so doing, provide improvements over the prior art that lacked the ability to adapt to user-specific conditions or states.

As a still further example, the present disclosure further describes biometric enabled virtual reality systems and methods configured to allow a user to appear in virtual space and/or as different from how they are in ordinary space. Each of these embodiments is further described herein.

More specifically, with respect to various embodiments, a biometric enabled virtual reality system is described herein. The biometric enabled virtual reality system is configured to detect one or more user intentions and to manipulate virtual avatar control based on the one or more user intentions for providing kinematic awareness in holographic, two-dimensional (2D) or three-dimensional (3D) virtual space. The biometric enabled virtual reality system comprises a biometric detection device configured to collect biometric signal data of a user. The biometric enabled virtual reality system further comprises a processor communicatively coupled to the biometric detection device. The biometric enabled virtual reality system further comprises a biometric software component comprising computational instructions configured for execution by the processor, the computational instructions, that when executed by the processor, causes the processor to determine, based on analysis of the biometric signal data of the user, a virtual representation of an intended motion of the user corresponding to an intention of muscle activation of the user. The computational instructions, that when executed by the processor, cause the processor to modulate, based on the virtual representation of the intended motion, virtual avatar control or output. The virtual avatar control or output may comprise manipulating a virtual avatar representing one or more aspects of at least one of the user or an object manipulated by the user in a holographic, virtual 2D space, or a virtual 3D space. The virtual avatar may be rendered by a virtual interface configured to provide the user a kinematic awareness in the holographic, virtual 2D space, or the virtual 3D space.

In additional embodiments, a biometric enabled virtual reality method is disclosed for detecting one or more user intentions and manipulating virtual avatar control based on the one or more user intentions for providing kinematic awareness in holographic, two-dimensional (2D), or three-dimensional (3D) virtual space. The biometric enabled virtual reality method comprises determining, based on analysis of a biometric signal data of a user, a virtual representation of an intended motion of the user corresponding to an intention of muscle activation of the user, the biometric signal data collected by a biometric detection device. The biometric enabled virtual reality method may further comprise creating a physiological profile of the user based on the biometric signal data of the user. The biometric enabled virtual reality method further comprises modulating, based on the virtual representation of the intended motion and by a biometric software component comprising computational instructions executed by a processor, virtual avatar control or output. The biometric enabled virtual reality method further comprises manipulating, based on the virtual avatar control or output, a virtual avatar representing one or more aspects of at least one of the user or an object manipulated by the user in holographic, virtual 2D space, or a virtual 3D space. The virtual avatar may be rendered by a virtual interface configured to provide the user a kinematic awareness in the virtual holographic, 2D space, or the virtual 3D space.

In still further embodiments, a tangible, non-transitory computer-readable medium stores instructions for detecting one or more user intentions and manipulating virtual avatar control based on the one or more user intentions for providing kinematic awareness in holographic, two-dimensional (2D), or three-dimensional (3D) virtual space. The instructions, when executed by one or more processors, cause the one or more processors to determine, based on analysis of a biometric signal data of a user, a virtual representation of an intended motion of the user corresponding to an intention of muscle activation of the user, the biometric signal data collected by a biometric detection device. The instructions, when executed by one or more processors, may further cause the one or more processors to create a physiological profile of the user based on the biometric signal data of the user. The instructions, when executed by one or more processors, further cause the one or more processors to modulate, based on the virtual representation of the intended motion and by a biometric software component comprising computational instructions executed by a processor, virtual avatar control or output. The instructions, when executed by one or more processors, further cause the one or more processors to manipulate, based on the virtual avatar control or output, a virtual avatar representing one or more aspects of at least one of the user or an object manipulated by the user in a holographic, virtual 2D space, or a virtual 3D space. The virtual avatar may be rendered by a virtual interface configured to provide the user a kinematic awareness in the holographic, virtual 2D space, or the virtual 3D space.

In additional embodiments, a biometric enabled virtual reality system is configured to detect one or more user intentions and to modulate virtual avatar control based on the one or more user intentions for creation of one or more virtual avatars or objects in holographic, two-dimensional (2D), or three-dimensional (3D) virtual space. The biometric enabled virtual reality system comprises a biometric detection device configured to collect biometric signal data of a user. The biometric enabled virtual reality system further comprises a processor communicatively coupled to the biometric detection device. The biometric enabled virtual reality system further comprises a biometric software component comprising computational instructions configured for execution by the processor, the computational instructions, that when executed by the processor, cause the processor to determine, based on analysis of the biometric signal data of the user, a virtual representation of an intended motion of the user corresponding to an intention of muscle activation of the user. The computational instructions, that when executed by the processor, further cause the processor to modulate, based on the virtual representation of the intended motion, virtual avatar control or output comprising creating at least one of a virtual avatar representing one or more aspects of the user or an object manipulated by the user in a holographic, virtual 2D space, or a virtual 3D space. The virtual avatar or object may be created in the holographic, virtual 2D space, or the virtual 3D space based on at least one of: (1) the biometric signal data of a user, or (2) user-specific specifications as provided by the user.

In still further embodiments, a biometric enabled virtual reality method is disclosed for detecting one or more user intentions and modulating virtual avatar control based on the one or more user intentions for creation of one or more virtual avatars or objects in holographic, two-dimensional (2D), or three-dimensional (3D) virtual space. The biometric enabled virtual reality method comprises determining, based on analysis of a biometric signal data of a user, a virtual representation of an intended motion of the user corresponding to an intention of muscle activation of the user, the biometric signal data collected by a biometric detection device. The biometric enabled virtual reality method may further comprise creating a physiological profile of the user based on the biometric signal data of the user. The biometric enabled virtual reality method further comprises modulating, based on the virtual representation of the intended motion and by a biometric software component comprising computational instructions configured for execution by a processor, virtual avatar control or output. The biometric enabled virtual reality method further comprises creating, based on the virtual avatar control or output, at least one of a virtual avatar representing one or more aspects of the user or an object manipulated by the user in a holographic, virtual 2D space, or a virtual 3D space. The avatar or the object may be created in the holographic, virtual 2D space, or the virtual 3D space based on at least one of: (1) the biometric signal data of a user, or (2) user-specific specifications as provided by the user.

In yet still further embodiments, a tangible, non-transitory computer-readable medium stores instructions for detecting one or more user intentions and modulating virtual avatar control based on the one or more user intentions for creation of one or more virtual avatars or objects in holographic, two-dimensional (2D), or three-dimensional (3D) virtual space. The instructions, when executed by one or more processors, cause the one or more processors to determine, based on analysis of a biometric signal data of a user, a virtual representation of an intended motion of the user corresponding to an intention of muscle activation of the user, the biometric signal data collected by a biometric detection device. The instructions, when executed by one or more processors, may further cause the one or more processors to create a physiological profile of the user based on the biometric signal data of the user. The instructions, when executed by one or more processors, further cause the one or more processors to modulate, based on the virtual representation of the intended motion and by a biometric software component comprising computational instructions configured for execution by a processor, virtual avatar control or output. The instructions, when executed by one or more processors, further cause the one or more processors to create, based on the virtual avatar control or output, at least one of a virtual avatar representing one or more aspects of the user or an object manipulated by the user in a holographic, virtual 2D space, or a virtual 3D space. The avatar or the object may be created in holographic, the virtual 2D space, or the virtual 3D space based on at least one of: (1) the biometric signal data of a user, or (2) user-specific specifications as provided by the user.

More generally, in various embodiments, biometric virtual reality and control systems and methods are described for the control and/or modulation of a virtual avatar. The biometric virtual reality and control systems generally comprise a biometric detection device that collects acceleration, inertia, orientation, and/or electromyographic information. The biometric detection device is coupled with a processor configured to detect an intention of a user (via biometric signals) to create movement from the user. If detected (i.e., movement is occurring), the processor may be configured to determine a body portion or portions (e.g., arm or leg) of the user and its current position in space about the user. Once calculated, virtual modulation or outputs regarding the current position in space about the user may be generated and provided to the patient, via a virtual interface or other interface, in the form of a kinematic awareness, proprioception, corporeal cue, or otherwise as described herein. The processor may execute a software program (e.g., a biometric software component) to categorize the characteristics of the biometric signals collected from the user. The categorization may then be used by the processor to either create, destroy, or modulate (e.g., control) a virtual avatar to represent the categorization of signals collected by the biometric enabled virtual reality system. The modulation of the virtual avatar may correspond to the biometric signals detected from the biometric detection device and rendered (e.g., via a virtual interface) in a visual fashion to embody the intended motion of the user. This may involve rendering an avatar that resembles an injured body component as if it weren't injured or amputated, and/or rendering an object such as the steering wheel of a car, a firearm, etc. The virtual avatar may then be displayed to the user through the visual field of the user and/or the user interface. For example, a user interface may be configured to provide real-time or near-real time modulation of the virtual avatar to closely represent the intended movements as produced by the user in real-time or near-real time.

As described herein the terms "virtual interface" and "user interface," used either alone or together, refer to a visual and/or a graphic interface (e.g., a graphic user interface (GUI)), rendered in either holographic, 2D, or 3D space via a display screen, via a projection (e.g., a holographic projector or a MICROSOFT MESH enabled device), or otherwise via a VR device, through which a user may view and/or interact with one or more biometric enabled VR systems and methods as described in various embodiments herein.

In various embodiments, the disclosure herein describes the use of both the virtual space—where a computer or processor generates an artificial or virtual image of one or more objects being projected to a user—and the ordinary space—where the user exists and performs his activities in the physical world. In various embodiments, the user in ordinary space has the capacity to create biometric signals with his or her muscles (e.g., through their body), such as an intention to activate one or more muscles which, when detected by a biometric device, allows the user to control or otherwise modulate a virtual avatar existing in virtual space. In such embodiments, the virtual interface and/or user interface, existing in virtual space, is configured to deliver a virtual user prompt and/or cue to the user with the purpose of instructing the user to perform a specific motion, action, or otherwise intention to activate one or more of their muscles within the ordinary space. Between the biometric signals and detected from the user within the ordinary space, the biometric enabled virtual reality systems and methods, as described herein, are capable of creating one or more modular effects on virtual avatar(s) in virtual or holographic space, in order to create, control, animate, or otherwise modulate the virtual avatar(s), as described herein.

In additional embodiments, a biometric virtual reality and control method is described regarding how a user profile is generated, updated, and maintained throughout a user interfacing with the systems and methods disclosed herein. The biometric virtual reality and control method comprises performing, by biometric software component executed by a processor communicatively coupled to a biometric detection device, an analysis of the user's biometric signals to create a profile based on the unique characteristics of the biometric signals unique to the user. These unique signals as analyzed may be associated with specific motions, periods of inactivity, or intention to perform a motion. Based on the analyzed signals, the biometric virtual reality and control method may be optimized to recognize similar, or deviations from, the analyzed signals as prompted in the virtual reality system. Furthermore, by the detected combination of one or more analyzed biometric signals, the systems and methods disclosed herein are able to determine a complex motion and related biometric signals of a specific user or patient. The biometric profile for the user comprises an electronic record of biosignal representations of user-specific biometric signal data, as stored in a computer memory.

In various embodiments, the biometric enabled virtual reality systems and methods described herein allow the user to modulate a virtual avatar and/or his or her virtual representation of biometric signal data in virtual space. In such embodiments, modulation of a virtual avatar may include, but is not limited to: size, shape, color(s), and/or a number of associated representations (e.g., multiple virtual avatars demonstrating simultaneous biometric signal representation). In such embodiments, the modulation of the virtual avatar may be initiated by the user through a user interface.

In various embodiments as described herein, the modulation, creation, and/or control of the virtual avatar may include, but is not limited to virtual bending, stretching, lifting, lowering, rotating, and/or otherwise moving the virtual avatar, and, in some aspects, according the specifications of the user, and/or as denoted by the biometric signal data analyzed by the processor and as collected by the biometric enabled virtual reality system described herein.

The representative embodiments of the present systems and methods disclosed herein provide numerous advantages over commonly used methods, such as mirror reflection or simple videography, in that the biometric enabled virtual reality systems and methods disclosed herein track the location (e.g., based on sensor location) of an uninjured or non-amputated body component as a reference. The biometric enabled virtual reality systems and methods disclosed herein provide an efficient and objective measurement technology wherein the user can receive virtual feedback, a kinematic awareness cue, kinematic cue, corporeal cue, personalized virtual representation, and/or a virtual representation of biometric signal data corresponding to the intention of activating a muscle group without the need for a camera or reference device. In various embodiments, the many novel features described herein result in a new method for creating or modulating a virtual avatar and/or determining the intention of movement of a body component of a user.

In various embodiments herein, kinematic awareness, corporeal awareness, and proprioception refer to the user's ability to detect in virtual space, via visual or tactile capabilities, one or more location(s) of a virtual avatar or object in reference to, or otherwise corresponding to, the user. In many of these embodiments, the detection of the virtual avatar or object may be superimposed over, or with, the user in virtual space, and/or may replace the location of a user's corporeal component in the event of an amputation. It is to be understood by persons having ordinary skill in the art that the user's awareness of the virtual avatar in space about the user, especially in the event of an amputation, greatly improves the user's ability to control or otherwise modulate the virtual avatar. In these embodiments still, the user's awareness of the virtual avatar further improves the capacity for the user to receive therapeutic benefits from said awareness, especially in cases when the user is presented with neurological pathologies, such as phantom limb pain. Further, the user's awareness, such as corporeal awareness, proprioception, or kinematic awareness of the virtual avatar in space about the user, may provide the user with a greater capacity to perform particular tasks in virtual space, for example, virtually typing on a keyboard, raising a glass, and/or inserting a key into a lock before rotating the key counter-clockwise.

In various embodiments, a user may perform an intention to activate a muscle or muscle group, thereby enabling the biometric enabled virtual reality system to detect and analyze an intention to activate a muscle or muscle group. The analysis of the intention to activate a muscle or muscle group, occurring regardless of whether or not the intention provided motion (e.g., in an extremity of the user), provides the biometric enabled virtual reality system with biometric data and information that correlates to a user's-specific intention to activate one or more muscles, and, thereby, the intention to control their virtual representation or avatar. Additionally, or alternatively, the biometric enabled virtual reality system and methods as described herein may store the analyzed intention as a key (e.g., reference and/or empirical data) to be referenced later against a subsequent analyzing of user biometric signal data. If a subsequent set of signals is substantially similar, having biometric significance in the analyzed characteristics in reference to the first set of biometric signal data, the biometric enabled virtual reality systems and methods may determine that an intention to activate one or more muscle groups may be similar to a previous intention.

In some embodiments, a subsequent set of biometric data may be added to a computer memory in combination with a first set of biometric data. In such embodiments, this creates more reference points for an additional, third, fourth, and/or $n^{th}$ data point or dataset, etc. In some embodiments, such collection of personalized user data can be used to modulate, control, create, or recreate the virtual avatar. Additionally, or alternatively, personalized user data may be used as reference data to identify how a virtual avatar should be modulated.

Moreover, a biometric enabled virtual reality system may be configured to track the progress, subjective inputs, and objective outputs (e.g., trending analysis of collected biosignals from a user) of a user by logging such data to create a user profile (e.g., a physiological profile of the user). The user profile may be configured to be accessed through or by authorized personnel. The access may be remote. The access by authorized personnel is especially useful for, and may be provided for, rehabilitation, patient compliance, and/or remote usage and monitoring purposes. Through the biometric enabled virtual reality system's capability of tracking a user's subjective symptoms, along with objective biometric signal data, the biometric enabled virtual reality system may track a user's progress from injury onset through rehabilitation, while enabling the simultaneous monitoring and tracking by a remote caregiver, provider, or otherwise authorized person(s). In many of these embodiments, the user profile may be modified, altered, or expanded upon by authorized person(s) to improve the experience of the user, such as through the modification of biometric signal data or diagnostic algorithms to better fit the dynamic and user-specific situation of the user.

Various embodiments of the present disclosure are described herein regarding the collection and categorization of biosignals or biometric information of a user. In such embodiments, the biometric enabled virtual reality systems and methods use the biosignals or biometric information to derive or create a virtual avatar that represents or categorizes characteristics of the biosignals or biometric information. The aforementioned categorization of biosignals or biometric information of a user may involve using analyzed data to create a user profile (e.g., a physiological profile), execute hardware and/or software commands, create customizable avatar modulation effects, and/or provide clinical recommendations based on the signal analytics to aid the user in improving performance or increase the yield of a desired outcome. The biometric enabled virtual reality systems and methods allow a user, through intention to move a muscle group, to control a virtual avatar, to initiate a kinematic awareness cue, to initiate a kinematic cue, or to initiate a corporeal cue, each of which either alone, or together, in various combinations, corresponding to the user's biometric signals. The biometric enabled virtual reality system may provide feedback on the user's intended motion, store the data from the user as biometric information in relation to the user's profile, detect specific motions conducted by the user, detect specific motions of the user to establish baseline readings, and store such information as reference information for empirical data analytics or as placeholders to reference against subsequent data collections. In general, the more biometric signal data and empirical data the virtual reality system collects for a user, the more precise the system becomes at determining when a user is intending to contract a muscle. The system, over time and with use, continues to gain precision and accuracy in identifying the intention to contract one or more muscle groups, specific to the user-generate biometric signals.

The biometric enabled virtual reality systems and methods as described herein may further comprise a user interface or virtual interface that allows the user to customize his or her virtual avatar, view information collected from the biometric detection device, modulate his or her personal appearance in virtual space, their personal appearance as depicted through the interpretation of the virtual avatar, and/or play games involving the virtual avatar. The user interface may be comprised of a display screen of a mobile or otherwise computing device being configured to display virtual images. The computing device may be communicatively coupled to a biometric detection device. The computing device may be communicatively coupled to the biometric detection device and a virtual reality immersive headset and/or an augmented reality system. The user interface may provide the user with prompts on what muscle movement intentions to perform, when, and how strong the user should initiate the muscle movement intention. Alternatively, the user may intend to perform a motion (activating neurons corresponding to one or more muscles), causing the system to decode the biometric signal data and identify the intention for an intended movement or activity, thereby initiating modulation, by a processor of computing device, of the virtual avatar or a related object in 2D, 3D, or holographic space.

A user interface or virtual interface may also prompt a user to input pain levels before and/or after using the biometric enabled virtual reality system or methods to track the user's pain development over periods of time as pain threshold data. The pain threshold data may then be used to optimize treatment times, types, and user prompts to better suit the user's specific condition to maximize the reduction in pain threshold as noted by the user. In various embodiments, collecting the pain threshold from the user may be used to provide recommendations on which motions should or should not be avoided. In continuance, the system or methods as describe herein may collect pain threshold data that correlates with the fatigue and physical exhaustion of the user, which may be used to tailor diagnostic algorithms to the physical capabilities of the user. Furthermore, the user's associated pain threshold information may be coupled with a software component (e.g., biometric software component) configured to display the user's biometric signal and pain threshold data over a secure web-based platform, allowing viewing and monitoring from a physician, caregiver, researcher, or otherwise authorized individual or group.

In accordance with the above, pain thresholds as input by the user may be used to optimize user prompts to better provide the user with a regimen suited towards their personal needs. For example, a user may perform shoulder flexion to 90 degrees, with 90 degrees of elbow flexion, followed by external rotation of the shoulder during an intention to contract one or more muscles, as initiated by the user. In this scenario, the user may experience a high level of pain. In response to this high level of perceived pain, the user may input their subjective interpretation of the level of pain experienced into the system. In subsequent events, the system may provide the user with a user prompt of similar characteristics, and the suggested motion may be sufficiently attenuated to prevent discomfort to the user, e.g., resulting in virtual interface output suggesting shoulder flexion of 45 degrees, 45 degrees of elbow flexion, and removal of the external rotation component. In various cases, depending on the pain thresholds as identified by the user, specific motions may be attenuated or completely avoided, as suggested by the virtual interface, and at the discretion of either the biometric enabled virtual reality system, the user, or second user (e.g., authorized personnel) having the capacity to influence user-specific aspects of the systems and methods disclosed herein. In these scenarios, the pain thresholds as experienced by the user may be stored within a computer memory in correspondence with the intended motion that initiated the onset of pain.

In many embodiments in accordance with the above, a pain threshold as experienced by a user may be detected through either a biometric detection device, optimized for collection of pain neurological signals from nociceptors of the user, or through a subjective questionnaire wherein the user may input their perceived levels of pain manually. In many of these embodiments, the pain threshold data may then be reviewed by a second user such as a clinician, physician, family member, or otherwise authorized user.

In some embodiments, the intention to move a muscle or muscle group of a user may consist of eccentric, concentric, isometric, or standard activation of one or more motor neurons innervating one or more muscle groups. In some embodiments, these intentions to move a muscle or muscle group are detected through one or more electromyographic electrodes, electrocardiogram electrodes, photodiodes, ultrasound sensors, accelerometers, inertial measurement units, electrooculogram sensors, infrared sensors, and/or one or more scleral search coils.

In some embodiments, a user's specific motion gesture (e.g., as prompted by the user interface), can be defined by, or selected from, a set of predetermined gestures in the user interface. The user may then be able to practice particular motions, track progress, and log pain thresholds for specific motion and/or gestures. In some embodiments, a training protocol with multiple prompted gestures or motions can be used to create a baseline for the user and/or add data to their biometric profile. Additionally, or alternatively, a gesture or motion intention may involve a voluntary action on behalf of the user or involuntary motion that is defined or simply performed by the user. In some embodiments, the user's specific motion gesture can be customized by the user, allowing the user to create his or her own custom gestures that can be provided back to the user in the form of prompts.

In continuance of the above, the user's specific motion gesture customization may include facets to duration, magnitude, frequency, location, or otherwise electromyographic signal data characteristics that influence how the system collects, analyzes, records, and/or outputs controls to modulate, control, and/or create the virtual avatar in accordance with the user's specific motion gesture customizations.

In accordance with the disclosure herein, the biometric enabled virtual reality systems and methods include improvements in computer functionality or in improvements to other technologies at least because the present disclosure recites that, e.g., a computing device, such as a wearable or mobile computing device, is enhanced by the biometric enabled virtual reality system as described herein. Through the coupling of traditional computer functionality and the biometric enabled virtual reality system, biometric signals are used to generate or control virtual avatars resulting in enhanced control of detection of virtual graphics. This benefit can be more readily available in devices that are configured to display a virtual avatar or otherwise a representation of the biometric signals of the user.

In various embodiments, a biometric detection system may be any combination of an implantable, wearable, and/or remote device. The components for the detection of biometric signals can be in contact with the user, subcutaneously positioned to the user, implanted within the user, within proximity to the user, or otherwise positioned with respect to a user to collect biometric and/or biosignal information of the user.

The biometric enabled virtual reality systems and methods described herein may comprise an adaptive learning model (e.g., a machine learning model) that is configured to identify user-specific intentions to activate one or more muscle groups based on at least one of any combination of collected biosignals, the user's unique user profile, empirically collected biometric data, and/or real time references from other biometric sensors collecting biosignal data of the user.

In various embodiments, user-specific intentions to activate one or more muscle groups (e.g., an actuated voluntary gesture) may comprise a resulting physical response of the user initiating an intention to activate one or more muscle groups. This voluntary intention on behalf of the user may be used to determine how the virtual reality avatar is modulated, such as controlled or created. In various embodiments, the biometric signal data and/or a virtual avatar based thereon, may be displayed on the user interface.

In various embodiments still, the inventive disclosure herein includes biometric enabled virtual reality systems and methods for determining an objective pain threshold of a patient. In such embodiments, a biometric detection device may collect biosignals from a patient, which may then be analyzed by the processor and stored in the memory. From these datasets, common mode signals of the user are detected and subtracted or filtered from the analytics, thereby removing any noise from motion, biometric detection device variance, atmosphere (e.g., light, radio wave interference, etc.). Once the dataset has been filtered of noise, the remainder of signal data, detected by the biometric detection device, is associated with nociceptor transmission electrical activity. These nociceptors, triggered by thermal, mechanical, chemical, or polymodal stimuli, are categorized by the frequency of electrical stimuli provided to the spinal cord and brain, along with signal data corresponding to characteristics within the signal data itself (e.g., amplitude, threshold values, etc.). Based on the frequency, amplitude, signal characteristics, and number of activated nociceptors, the processor may then determine for the user an objective pain measurement. In various embodiments, the objective pain measurement may then be provided to a second user, having an authorized capacity to view and otherwise influence biometric and/or biosignal data as collected from the user and/or the user profile. In these embodiments, the second user may also have the capacity to communicate with the user, and in the event the user is receiving medical treatment, provide the user with medical advice and/or modulate the system's user motion prompt algorithms.

In some of the various embodiments still, the biometric detection device may be optimized to collect biosignal data from nociceptor cells within the user. Such cells may provide biosignals that relate to pain threshold and perception, and may comprise data defining a user's physiological profile.

In various embodiments, a user may be prompted through a user interface to perform a muscle action, intention, motion, or gesture. In these embodiments, the intention to activate one or more muscles on behalf of a user, especially subsequent to a user-prompt or cue, e.g., via a user interface or virtual interface, may be linked to a specific activity as mentioned above. Such intentions, gestures, or complex motions may be decoded from the biometric signals as collected by the biometric detection device. Such gestures, being symbolic towards an intended activation of one or more muscle groups specific to the user, may be motions readily understood by the user (e.g., "thumbs up", "wave", "clench fist", etc.).

In accordance with the above, and with the disclosure herein, the present disclosure includes improvements in computer functionality or improvements to other technologies at least because the present disclosure recites that, e.g., a computing device, such as a wearable computing device or a virtual reality system, is enhanced via the biometric software or other components herein that allow for the enhanced control within a virtual reality system of a virtual avatar via the biometric detectors and processing algorithms that create user-specific profiles. That is, the present disclosure describes improvements in the functioning of the computer itself or "any other technology or technical field" because a computing device, such as a wearable device or a virtual reality system, can be updated or enhanced to provide more accurate control of avatars or the detection of biometric signals, which can then be used for therapeutic treatments for patients that have neurological ailments. This improves over the prior art at least because the systems and methods herein provide for a faster and/or more efficient way of measuring the biometric signals from a user and using such signals to modulate a virtual reality system avatar.

The present disclosure relates to improvement to other technologies or technical fields at least because the systems and methods disclosed herein allows a biometric detection system to modulate, such as control or create, a virtual avatar with the intention to move one or more muscles at greater accuracy and efficiency than conventional techniques, especially where the systems and methods disclosed herein involve creating a user-specific profile to better determine when a user is initiating the intention to move one or more muscles, and when reacting with virtual objects. The advantages of the systems and methods disclosed herein become even more apparent when a user has a unique and specific ailment, physical incapacity, personal social requirement (e.g., to visually appear to the user's unique specification in virtual space), or physiological condition wherein traditional methods are inadequate.

In addition, the present disclosure includes applying certain aspects or features, as described herein, with, or by the use of, a particular machine, e.g., a wearable biometric device or other similar device to provide a collection of biometric signals from the user to a processor for the input into a biometric enabled virtual reality system.

The present disclosure includes effecting a transformation or reduction of a particular article to a different state or thing, e.g., transformation or reduction of biometric signals of a user into a medium easily used to create a user-specific profile and/or virtual avatar, thereby enabling the improved upon control of the virtual avatar.

The present disclosure includes specific features other than what is well-understood, routine, conventional activity in the field, or adding unconventional steps that confine the claim to a particular useful application, e.g., biometric enabled virtual reality systems and methods for providing improved detection of biometric signals of a user and configured to use the associated biometric signals in the form of biometric data to modulate a virtual avatar.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed therein. It should be understood that each Figure depicts an embodiment of a particular aspect of the disclosed system and methods, and that each of the Figures is intended to accord with a possible embodiment thereof. Further, whenever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIG. 1A further illustrates a biometric enabled virtual reality system configured to detect one or more user intentions and to modulate virtual avatar control based on the one or more user intentions for creation of one or more virtual avatars or objects in holographic, two-dimensional (2D), or three-dimensional (3D) virtual space, in accordance with various embodiments herein.

DETAILED DESCRIPTION

Figure 1A:
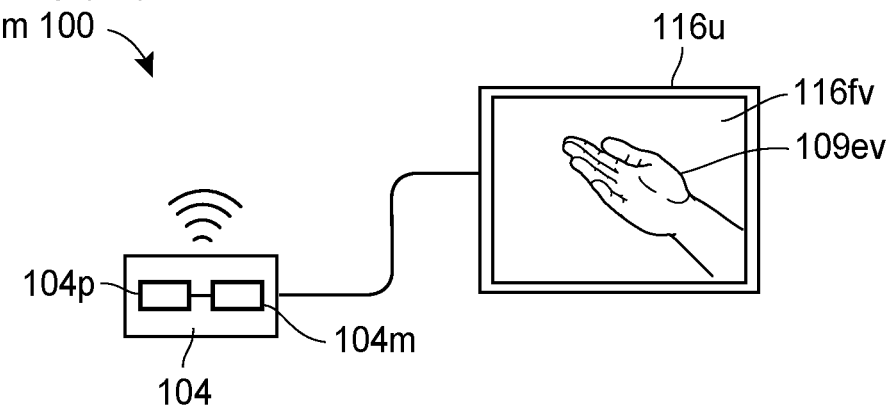
FIG. 1A illustrates an example biometric enabled virtual reality system configured to detect one or more user intentions and to manipulate virtual avatar control based on the one or more user intentions for providing kinematic awareness in holographic, two-dimensional (2D), or three-dimensional (3D) virtual space, in accordance with various embodiments herein.
Figure 1A:
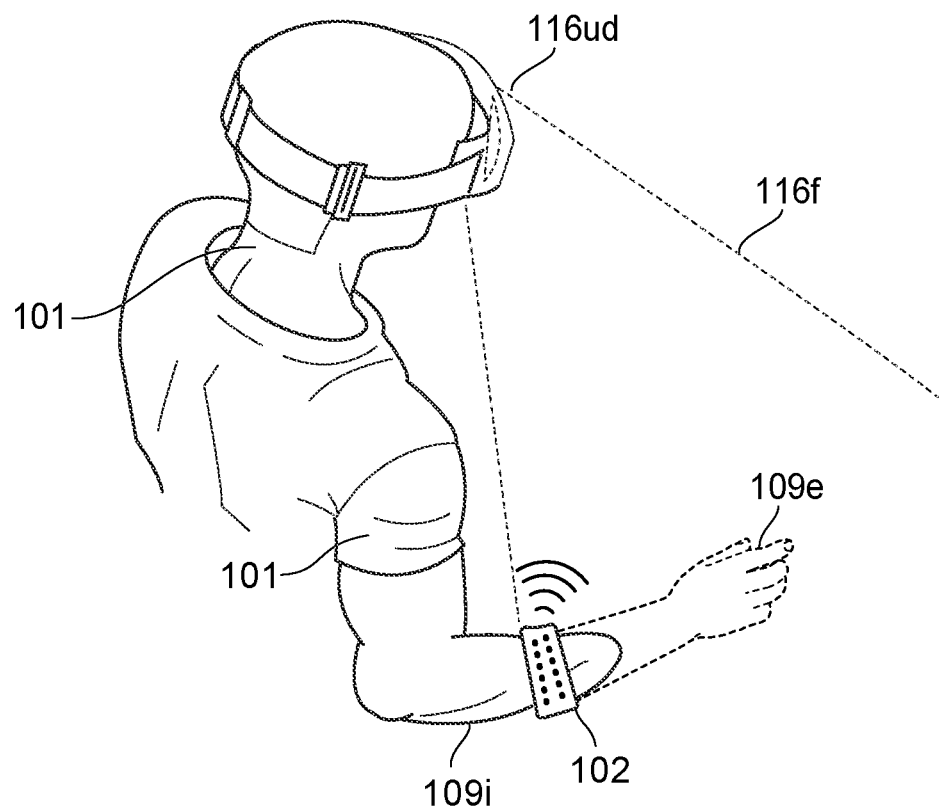

While the systems and methods disclosed herein is susceptible of being embodied in many different forms, it is shown in the drawings and will be described herein in detail specific exemplary embodiments thereof, with the understanding that the present disclosure is to be considered as an exemplification of the principles of the systems and methods disclosed herein and is not intended to limit the systems and methods disclosed herein to the specific embodiments illustrated. In this respect, before explaining at least one embodiment consistent with the present systems and methods disclosed herein in detail, it is to be understood that the systems and methods disclosed herein is not limited in its application to the details of construction and to the arrangements of components set forth above and below, illustrated in the drawings, or as described in the examples. Methods and apparatuses consistent with the systems and methods disclosed herein are capable of other embodiments and of being practiced and carried out in various ways. Also, it is to be understood that the phraseology and terminology employed herein, as well as the abstract included below, are for the purposes of description and should not be regarded as limiting.

FIG. 1A illustrates an example biometric enabled virtual reality system 100 configured to detect one or more user intentions 109i and to manipulate virtual avatar control (e.g., of virtual avatar 109ev) based on the one or more user intentions for providing kinematic awareness in holographic space, two-dimensional (2D), or three-dimensional (3D) virtual space, in accordance with various embodiments herein. FIG. 1A further illustrates a biometric enabled virtual reality system configured to detect one or more user intentions 109i and to modulate virtual avatar control based on the one or more user intentions for creation of one or more virtual avatars or objects (e.g., virtual avatar 109ev) in holographic, two-dimensional (2D), or three-dimensional (3D) virtual space, in accordance with various embodiments herein.

In various embodiments, biometric enabled virtual reality system 100 is configured to provide a kinematic awareness cue to the user in response to biometric signal data that is received from a biometric detection device (e.g., biometric detection device 102). Additionally, or alternatively, biometric enabled virtual reality system 100 is configured to modulate (e.g., create or control) virtual avatar control in holographic, 2D, or 3D virtual space.

FIG. 1A depicts a user 101 interfacing with biometric enabled virtual reality system 100 while controlling a virtual avatar (e.g., virtual avatar 109ev) corresponding to a missing extremity 109e of the user 101 (e.g., a phantom limb, such as an amputated limb, malformed limb, or otherwise non-whole extremity of the user 101). The user is viewing the virtual avatar (e.g., virtual avatar 109ev) via a user interface 116u of a user interface device 116ud. The biometric enabled virtual reality system 100 comprises a biometric detection device 102 (e.g., a biometric detector) configured to collect biometric signal data from the user's body. The user's field of view 116f is mapped to, or configured to correspond with, the user interface 116u to create or display a virtual field of view 116fv. The virtual field of view 116fv is displayed via the user interface 116 and contains, renders, or depicts the virtual avatar (e.g., virtual avatar 109ev) as depicted, superimposed over the user's injured body component (e.g., an amputated arm in the example of FIG. 1A) in holographic space, virtual 2D space, or virtual 3D space. For example, virtual avatar 109ev may be displayed on a display screen in 2D space (e.g., as rendered as 3D image in 2D space). Additionally, or alternatively, virtual avatar 109ev may be displayed or rendered in 3D space, e.g., via a VR headset. Additionally still, the virtual avatar 109ev may be depicted as a holographic image; appearing as a 2D or 3D image in the ordinary space as demonstrated by either a holographic projector or VR headset (e.g., a MICROSOFT MESH enabled device).

In the example of FIG. 1A, user interface device 116ud comprises a VR headset. The VR headset may comprise a VR headset such as OCULUS VR headset, an HP REVERB VR headset, a VALVE INDEX VR headset, a SONY PLAYSTATION VR headset, an HTC VIVE VR headset, a MICROSOFT MESH headset, or the like. In such embodiments, user interface 116u comprises a display screen of the VR headset as attached or included as part of the VR device (e.g., user interface device 116ud), where user interface 116u comprise a graphic user interface (GUI) capable of rendering VR graphics or images in virtual space via the user interface 116u of the VR headset.

Additionally, or alternatively, user interface device 116ud be or may further comprise a mobile device (e.g., a computing device 104), such as a cellular phone, tablet device, etc. such as an APPLE IPHONE or GOOGLE ANDROID device. In such embodiments, the user interface 116u comprises a display screen of the mobile device as attached or included as part of the mobile device, where the user interface 116*u* comprises a graphic user interface (GUI) capable of rendering VR graphics or images on the display screen of the mobile device. For example, interface device 116*ud* may be an APPLE IPHONE or GOOGLE ANDROID device having a display screen for rendering VR graphics or images on user interface 116*u* via, e.g., a GOOGLE CARD-BOARD device and related app software as implemented on the mobile device, or the like.

In various embodiments, user interface device 116*ud* comprises, or is communicatively coupled to, one or more processors (e.g., a processor 104*p*), for executing computing instructions for rendering VR graphics or images, or for implementing any algorithms, methods, flowcharts, etc. as described herein. In addition, the interface device 116*ud* comprises, or is communicatively coupled to, one or more computer memories (e.g., a memory 104*m*), for storing instructions for rendering VR graphics or images, or for implementing any algorithms, methods, flowcharts, etc. as described herein. In various embodiments, the one or more computer memories 104 may comprise tangible, non-transitory computer-readable medium (e.g., RAM or ROM) for storing instructions, graphics, images, or the like.

In the embodiment of FIG. 1A, a computing device 104 comprises processor 104*p* communicatively coupled to memory 104*m*. In the depicted embodiment, processor 104*p* is communicatively coupled (via wireless signals) to biometric detection device 102. Wireless signals may comprise any one or more of IEEE 802.11 wireless signals (WIFI), BLUETOOTH signals, or the like. Additionally, or alternatively, processor 104*p* may be communicatively coupled via wired signals, e.g., via a USB or similar wired connection (not shown) to biometric detection device 102.

In various embodiments, biometric enabled virtual reality system 100 includes software components (e.g., biometric software component 107) that comprise computing instructions executable by a processor (e.g., processor 104*p*), and which may be computing instructions implemented in programming languages such as, e.g., C, C++, C#, Java, Python, Ruby, R, or the like. The software component may be stored on a memory (e.g., memory 104*m*) communicatively coupled (e.g., via a system-on-a-chip (SoC) and/or computing bus architecture) to one or more processors (e.g., processor 104*p*). Processor 104*p* may be an ARM, ATOM, INTEL based processor, or other similar processor (e.g., as typically used with wearable or similar devices) for executing the computing instructions, applications, components, algorithms, source code, or otherwise software (e.g., of software component) as depicted or described herein for various methods.

Execution of the computing instructions of a software component by the processor 104*p* causes the processor 104*p* to perform an analysis of the biometric signal data (e.g., biometric signals and/or data 103, 110, and/or 110*i*) of the user 101 as detected by the biometric detection device 102. For example, software component (stored in the memory 104*m*) may contain computing instructions executable by the processor 104*p*. The computing instructions may be compiled to execute on a processor (e.g., processor 104*p*) or may be otherwise be configured to be interpreted or run by the processor 104*p*. Such computing instructions may be coded to execute the algorithms, such as the methods and/or flowcharts as described herein. For example, computing instructions of a software component (e.g., stored in memory 104*m*) may comprise one or more event listeners, such as a listener function programmed to detect and/or receive biometric signal data of user e.g., biometric signals and/or data 103, 110, and/or 110*i*) as detected and/or received from the biometric detection device 102. In this way, the biometric signal data of the user 101 would be pushed to, or otherwise received from, biometric detection device 102 for detection or generation of biometric signal data that would trigger the listener function to provide such biometric data for use for virtual avatar or object modulation (e.g., such as creation or control of a virtual avatar and/or an object) and/or as described for one or more portions the methods or algorithms of FIG. 3, FIG. 4, and/or FIG. 5, or otherwise, as described herein.

It is to be understood that processor 104*p* and/or memory 104*m* may be differently configured, arranged, and/or coupled with respect to any of biometric detection device 102, user interface device 116*ud*, and/or user interface 116*u*. For example, additionally, or alternatively, processor 104*p* and/or memory 104*m* may be incorporated into a medical device, such as prosthetic device, or other computing device communicatively coupled to biometric detection device 102, user interface device 116*ud*, and/or user interface 116*u*, and configured to operate as part of biometric enabled virtual reality system 100 and/or to implement biometric enabled virtual reality method(s) as described herein. For example, each of the biometric detection device 102 (with its various sensors, as positioned with respect to the user), processor 104*p*, memory 104*m*, user interface device 116*ud*, user interface 116, etc. may be communicatively coupled to one another via a system-on-a-chip (SoC) architecture or other electronic architecture or interface, which may comprise a computing device (e.g., computing device 104) that includes hardware (e.g., processor 104*p*) of biometric enabled virtual reality system 100 of and/or software (e.g., computing instructions as stored in memory 104*m*) for implementing the biometric enabled virtual reality methods as described herein.

Additionally, or alternatively, biometric detection device 102, processor 104*p*, memory 104*m*, and/or other user interface 116*u* may be part of separate computing devices, which are communicatively coupled, e.g., via a wired or wireless connection. For example, in one embodiment, user interface 116*u* may be implemented on a separate or remote computing device (e.g., a laptop or computer) in wireless communication (e.g., BLUETOOTH protocol or WIFI (802.11) standard) with the biometric enabled virtual reality system 100, where a user configures the biometric enabled virtual reality system 100 (e.g., by training or otherwise configuring the biometric enabled virtual reality system 100, user interface 116*u*, or biometric detection device 102 components and configuration as described herein) via the remote user interface 116*u* on the separate computing device. A biometric enabled virtual reality apparatus manager, comprising computing instructions, etc., may also be implemented or configured on separate computing device, to implement or control the biometric enabled virtual reality systems and methods described herein.

With reference to FIG. 1A, biometric enabled virtual reality system 100 comprises a biometric detection device 102 configured to collect biometric signal data of user 101. In various embodiments, biometric detection device 102 may include least one of (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, (j) one or more accelerometers, and/or (k) one or more scleral search coils.

Additionally, or alternatively, biometric detection device 102 may at least be one of an implantable device (e.g. implanted on or within a user's body and/or skin); a wearable device (e.g. such as a watch, arm band, leg band, an arm cuff, etc.); or remote detection device (e.g., such as a remote control, or other device cable of sensing biometric signals of a user). For example, in the embodiment of FIG. 1A, biometric detection device 102 is a wearable device on user 101's arm.

Biometric detection device 102 may be configured to be at least one of: subcutaneously positioned with respect to the user 122, in superficial contact with the user 120, subdermally or implanted within the user 121, and/or within a proximity to the user 119. The biometric signals and/or biometric data 103 may then be analyzed by the processor 104*p*, to create a virtual avatar 109*ev* and, in similar embodiments, superimpose the virtual avatar 109*ev* over the amputated extremity (e.g., extremity 109*e*) of the user (e.g., user 101) to provide a kinematic awareness cue within the virtual visual field of the user 116*fv*.

Figure 1B:
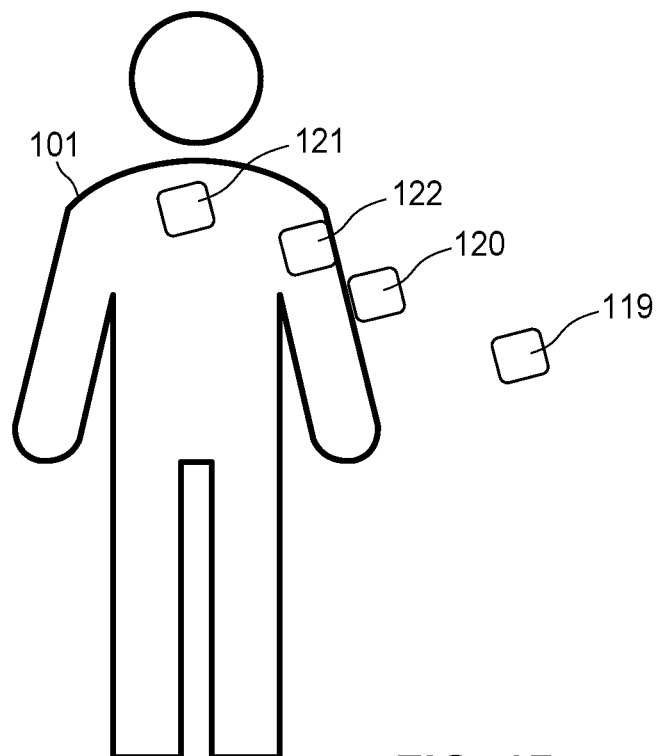
FIG. 1B is a diagram depicting one or more location(s) of biometric sensors positioned relative to a user for collection of biometric signal data of the user, the positioning comprising in proximity to the user, in superficial contact with the user, subcutaneously positioned to the user, or subdermally planted within the user, in accordance with various embodiments herein.
Figure 1C:
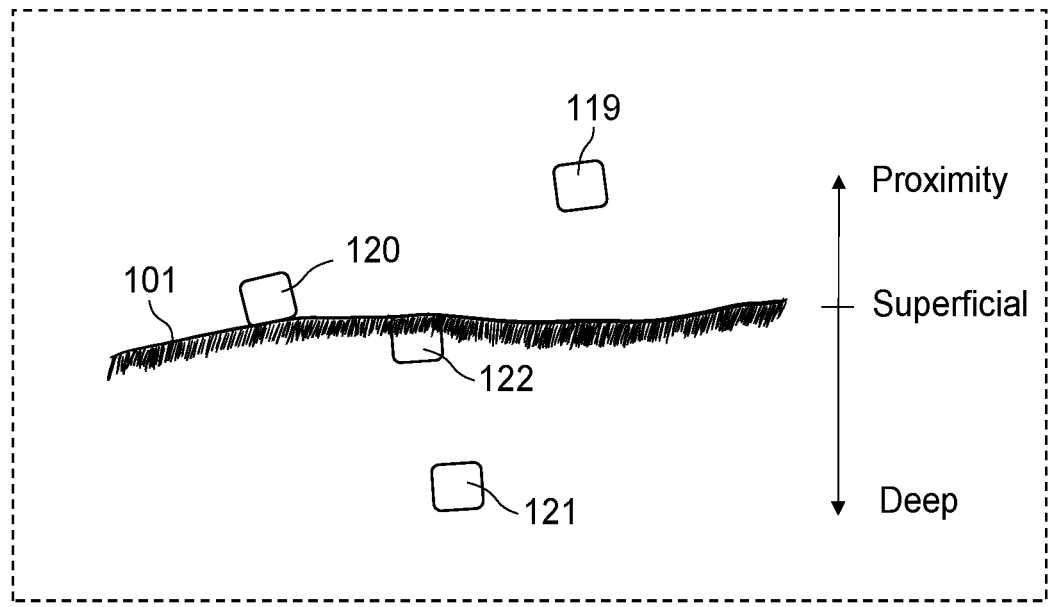
FIG. 1C is a further diagram depicting the one or more location(s) of biometric sensors as described for FIG. 1B and positioned relative to a user for collection of biometric signal data of the user, the positioning comprising in proximity to the user, in superficial contact with the user, subcutaneously positioned to the user, or subdermally planted within the user, in accordance with various embodiments herein.

By way of non-limiting example, FIGS. 1B and 1C each depict diagrams depicting one or more location(s) of biometric sensors of a biometric detection device 102 positioned relative to a user for collection of biometric signal data of the user, the positioning comprising in proximity to the user, in superficial contact with the user, subcutaneously positioned to the user, or subdermally planted within the user, in accordance with various embodiments herein. As illustrated by FIGS. 1B and 10, sensors of a biometric detection device 102 may be situated in at least one of (a) proximity to a user 119, (b) superficial contact to a user 120, (c) subcutaneously positioned to a user 122, and/or (d) subdermally planted within a user 121. In some embodiments, sensors positioned according to one or more of the positioning types 119-122 may be used to collect the biometric signals from a user 101.

Certain advantages as to data fidelity and user-specific control, modulation, avatar creation, and otherwise are achieved through various sensor placements and locations, as illustrated by FIGS. 1B and 10. For example, the location(s) of the biometric sensors allow biometric detection device 102 to collect biometric signal data of a user at different and/or various intensities or types, and/or at different and/or various fidelities to provide increased accuracy and/or different qualities of biometric signal data. Such increased accuracy and/or different qualities of biometric signal data provide the virtual reality systems and methods described herein with exact or specific (e.g., user-specific) biometric signals or data in order to allow for precise and/or user-specific modulation, control, creation of virtual avatars or objects, as described herein.

Figure 2A:
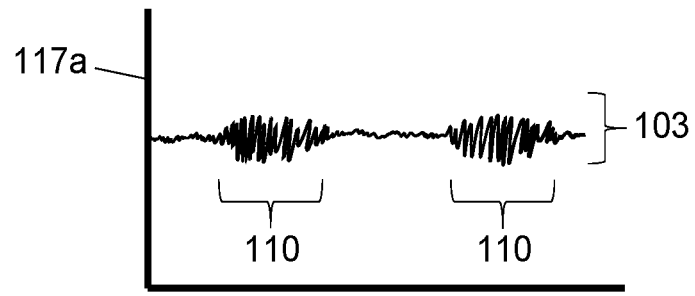
FIG. 2A is a diagram illustrating a first set of biometric data and/or signals of a user that may be collected by the example biometric enabled virtual reality system of FIG. 1A, in accordance with various embodiments herein.
Figure 2B:
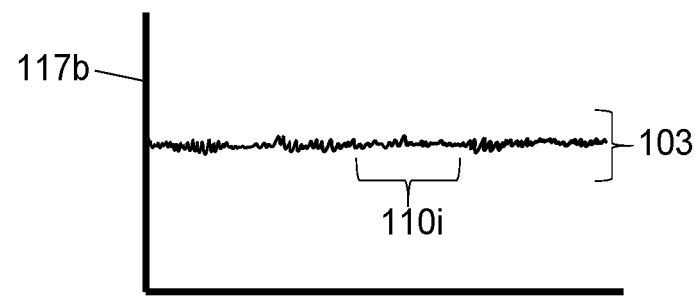
FIG. 2B is a diagram illustrating a second set of biometric data and/or signals of a user that may be collected by the example biometric enabled virtual reality system of FIG. 1A, in accordance with various embodiments herein.
Figure 2C:
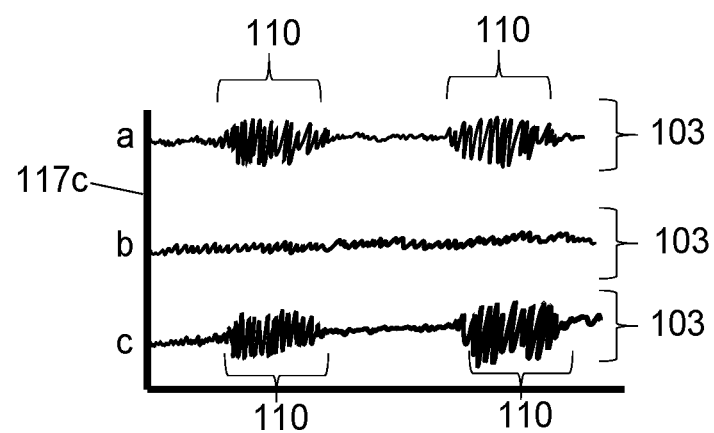
FIG. 2C is a diagram illustrating a third set of biometric data and/or signals of a user that may be collected by the example biometric enabled virtual reality system of FIG. 1A, in accordance with various embodiments herein.

FIGS. 2A-2C illustrate diagrams (e.g., diagrams 117*a*, 117*b*, and 117*c*) of sets of biometric data and/or signals of a user (e.g., user 101) that may be collected by the example biometric enabled virtual reality system of FIG. 1A. In particular, FIG. 2A is a diagram 117*a* illustrating a first set of biometric data and/or signals of a user (e.g., user 101) that may be collected by the example biometric enabled virtual reality system of FIG. 1A, in accordance with various embodiments herein. Similarly, FIG. 2B is a diagram 117*b* illustrating a second set of biometric data and/or signals of a user (e.g., user 101) that may be collected by the example biometric enabled virtual reality system of FIG. 1A, in accordance with various embodiments herein. In addition, FIG. 2C is a diagram 117*c* illustrating a third set of biometric data and/or signals of a user (e.g., user 101) that may be collected by the example biometric enabled virtual reality system of FIG. 1A, in accordance with various embodiments herein.

Biometric detection device 102, with its various sensors (e.g., positioned relative to user 101 as described herein for FIGS. 1B and/or 10) may collect biometric data and/or signals of user 101. For example, as shown in FIG. 1A, biometric data and/or signals 103 are collected from the injured body component (e.g., amputated arm) of user 101. It is to be understood, however, that biometric data and/or signals may be collected from of a user at additional, or different, body components (e.g., either injured or non-injured), for example, at a user's leg, ankle, foot, arm, neck, head, and/or other body part and/or extremity. More generally, FIGS. 2A-2C demonstrate non-limiting different types of biometric data and/or signals that may be collected from a user (e.g., user 101), as used to create a user-specific profile (e.g., a physiological profile of a user) in relation to detected intentions of the user upon intending to activate one or more muscle groups of the user.

FIGS. 2A-2C further illustrate examples of biometric signals and/or data 103, 110, and/or 110*i* as detected for a user (e.g., user 101) and the user's intention to activate (or not activate) one or more muscles. In particular, FIGS. 2A-2C demonstrate examples where a biometric detection device (e.g., biometric detection device 102) in superficial contact 120 with user 101, for example, as shown for FIG. 1A. As shown for each of diagrams 117*a*-117*c* of FIGS. 2A-2C, biometric signals 103 of the user are received from the biometric detection device 102. Such biometric signals 103 may be filtered or processed to become biometric data. As described herein, biometric signals and/or biometric data 103, 110, and/or 110*i* may be referred to interchangeably herein as biometric data, biometric signals, biometric signal data, biometric filtered signals, biometric filtered data, and the like. Such biometric signals may be analyzed by a processor (e.g., processor 104*p*) for the presence of one or more user intentions to activate corresponding one or more muscles. For example, diagrams 117*a* and 117*c* each illustrate biometric signal portions 110 that may be determined by processor 104*p* as indicating the presence of one or more user intentions to activate corresponding one or more muscles. The biometric signal portions 110 may represent an increased or intensified signal and/or data activity (as compared to a baseline non-activity) of the user's detected biometric signal data corresponding to the one or more user intentions to activate the user's one or more muscles. For example, the presence of the intention(s) to activate one or more muscles is created by the user 101 attempting to perform a motion (e.g., typically in response to a user motion prompt 124), while in biometric contact with the biometric detection device 102.

FIG. 2B (diagram 117*b*) demonstrates a series or set of idle biometric signals and/or data 110*i* of a user (e.g., user 101). Such signals may be received when the user is a rest. Such signals may be useful in generating or performing a baseline of the user (e.g., non-activity of a user). The baseline may be used as part of the user's physiological profile, which is user-specific to the user. Together, biometric signals and/or data 103, 110, and/or 110*i* may be used to define or otherwise represent a user-specific intention to activate one or more muscles, and may be used in the analysis to determine whether or not the intention to activate one or more muscles is present.

FIG. 2C (diagram 117*c*) demonstrates multiple series or sets (set a, set b, and set c) of biometric signals and/or data (e.g., biometric signals and/or data 103, 110, and/or 110*i*) of a user (e.g., user 101). Each of the sets a, b, and c may be generated by different sensors of biometric detection device 102, such as sensors as differently positioned as described herein by FIGS. 1B and/or 10. In some embodiments, the biometric signals and/or data 103, 110, and/or 110*i* may be combined (e.g., averaged, summed, etc.) to provide an overall signal of the user for modulation, control, creation, and/or other determinations or processing (e.g., by processor 104*p*) as described herein. Additionally, or alternatively, the biometric signals and/or data 103, 110, and/or 110*i* may be separately processed (e.g., by processor 104*p*) for modulation, control, creation, and/or other determinations or processing as described herein.

It is to be understood that biometric signals and/or data 103, 110, and/or 110*i* may be of analogue and/or digital form, where processor 104*p* may be configured to analyze one or both analogue and/or digital signals. For example, in various embodiments processor 104*p* may be configured to receive analogue or raw signal data of a user as detected by biometric detection device 102. Processor 104*p* may be configured to receive biometric signal data in digital form as processed or pre-processed by biometric detection device 102. Still further, additionally, or alternatively, processor 104*p* may receive analogue or raw signal data of a user as detected by biometric detection device 102 and process or filter such data to create digital data for additional use, analysis, determination, or as otherwise described herein. In some embodiments, for ease of reference, the term "biometric signals" may be refer to either or both of analogue or raw signal data of a user as detected by biometric detection device 102, and the term "biometric data" may refer to digital data as determined based on filtering and/or processing, by processor 104*p*, of analogue or raw signal data of a user. However, it is to be understood that such terms may be used interchangeability herein.

Biometric signals and/or data 103, 110, and/or 110*i*, as described for FIGS. 2A-2C, illustrate the diversity of data collected from biometric detection device 102. In various embodiments, biometric signals and/or data 103 may comprise electromyographic data (EMG). FIGS. 2A-2C demonstrate the biometric signals collected from a variety of, but non-limiting, biometric detection device 102 configurations. In FIGS. 2A and 2C, the biometric signals which may be stored in the memory 104*m* as biometric signal data, demonstrate the user's intention to activate one or more muscles (e.g., as determined or detected from biometric signals and/or data 110). In each of FIGS. 2A-2C, the biometric signals and/or data (e.g., biometric signals and/or data 103, 110, and/or 110*i*, whether filtered or non-filtered) are recorded over time (x-axis) and may be compared against the amplitude, frequency, and/or magnitude of biometric signals detected by the biometric detection device 102 (y-axis). Diagram 2C demonstrates two separate intentions (intentions a and c) to activate one or more muscles (e.g., as determined or detected from biometric signals and/or data 110) between moments of idle behavior (behavior b) on behalf of the user (e.g., user 101) to activate one or more muscles that correspond with the biometric detectors detecting biometric signals. FIG. 2B demonstrates biometric signal data 103 collected from a user (e.g., user 101) that is currently collecting idle biometric signals. Based on the contents of the signals collected from FIG. 2B, the processor 104*p* may determine after an analysis of muscle intention (e.g., analysis of muscle intentions 112 as described for FIGS. 4 and 5 herein) that the user 101 has not intended to activate one or more muscles (e.g., as determined or detected from biometric signals and/or data 110*i*). The biometric signal data 103 as illustrated in FIGS. 2A-2C, demonstrates a non-limiting and specific configuration of biometric sensors detected by the biometric detection device 102 at a given time period.

Additionally, or alternatively, FIGS. 2A-2C may each represent separate channels, which may each being individual biometric sensors (channels of data) that independently provide biometric signals from different locations around the user 101. While the user (e.g., user 101) initiates an intention to activate one or more muscles (e.g., as determined or detected from biometric signals and/or data 110), the biometric detection device 102 may temporally record the biometric signals from or of the user (e.g., user 101) from across leads or sensors, for example as described herein for FIGS. 1B and/or 10. Based on the biometric signal data 103, 110, and/or 110*i* recorded, the biometric signals from leads or sensors may be used to determine intentions to activate one or more muscles (e.g., as determined or detected from biometric signals and/or data 110 by processor 104*p*), respectively. In some instances, the biometric sensor recording data from a lead or sensor (e.g., as illustrated for FIG. 2B) may not pick up any intentions to activate one or more muscles (e.g., as would be determined or detected from biometric signals and/or data 110*i*), and the associated muscles would be considered to be idle as described herein.

Furthermore, FIGS. 2A-2C demonstrate a range of measurement fidelity of biometric detection device 102 with respect to biometric signals of user 101. Such measurement fidelity may include multiple different locations about the user (e.g., as described for FIGS. 1B and 10), which may or not be temporally in tandem. Leads or sensors (e.g., as described for FIGS. 1B and 10) may detect signals indicating the intention to activate one or more muscles (e.g., as determined or detected from biometric signals and/or data 110) in a similar temporal fashion. Based on the configuration of the biometric enabled virtual reality system 100, e.g., as determined by the user 101 in user interface 114 as described herein for FIG. 3, processor 104*p* may determine that the intentions to activate one or more muscles (e.g., as determined or detected from biometric signals and/or data 110) correlate with a specific user muscle contract, motion, or intention. This information may then be used by the processor 104*p* to determine the extent to which the virtual avatar 109*ev* is to be modulated, created, controlled, or otherwise determined in order to render or display virtual representation of the intended motion. In comparison, the biometric signal data in FIG. 2B illustrates the user (e.g., user 101) being idle, or not otherwise generating biometric signals to an extent that would indicate the intention to not activate one or more muscles (e.g., as determined or detected from biometric signals and/or data 110*i*).

Conversely, FIG. 2C may demonstrate the intention to activate one or more muscles (e.g., as determined or detected from biometric signals and/or data 110), whether or not the user (e.g., user 101) is able to actively move the muscles they are intending to activate. Because the biometric signals generated by the user (e.g., user 101), and as detected by the biometric detection device 102, are not necessarily determinate that a motion is taking place, the user (e.g., user 101) may be intending to activate one or more muscles (e.g., as determined or detected from biometric signals and/or data 110) but unable to create the motion they are intending to conduct. Processor 104*p* may determine that the intention to activate one or more muscles (e.g., as determined or detected from biometric signals and/or data 110) is indicated through the biometric signal data 103 and/or 110 that is received by the biometric device 102, and initiate the process to create or determine a virtual representation of the intended motion 108vr irrespective of whether or not the user (e.g., user 101) was able to create the intended motion.

Still further, FIGS. 2A-2C illustrate biometric signal data as received (over time and recorded as signal data in the memory 104m, temporally, or in segments), identified, or as otherwise detected when a user (e.g., user 101) is active, e.g., performing a gesture, motion, or intention to activate a muscle or a group of muscles to perform an action, such as a user motion prompt 124 as described herein. Biometric signal data is detected over time via the biometric detection device 102 temporally, as described herein, at various biometric signal strengths, which is as a whole, indicates a data pattern that defines or represents a user-specific or user selected motion, including, e.g., in response to a user motion prompt 124. In various embodiments, such data pattern may be used to generate, record, create, provide, or otherwise implement a given user-specific configuration, as controlled by the user-interface 116u, in order to configure the biometric detection device 102, initial profile 114, or user interface device 116ud for specific use by the user. In some embodiments, such detection of biometric signal data may cause processor 104p to initiate a modulation of a virtual avatar, or otherwise create alternate visual cue to help the user 101 with the proprioception of virtual avatars about the user's 101 current space, as depicted in the virtual visual field of the user 116fv in either holographic, 2D, or 3D virtual space.

In the examples of FIGS. 2A-2C, in some embodiments, a motion intention of the user (e.g., user 101), e.g., flexing the arm at the elbow, may create biometric signals that are consistent with recorded biometric signal data (e.g., as previously recorded in memory 104m). Such motion intention may be conducted on behalf of the user that is separate from another motion intention. As illustrated for FIG. 2D, the flexion at the elbow motion may be combined with the supination and/or pronation of the wrist. As a whole and in a sequence, these user-specific and user-selected motions may be used by the processor 104p to generate or determine virtual representation of the intended motion 108vr In some embodiments, the virtual representation will move virtual avatar 109ev in holographic space or virtual space, e.g., as visible via user-interface 116u.

Additionally, or alternatively, a user-specific motion may be defined as one or more unique motions or motion intentions as defined by the user, e.g., by configuration via the user-interface 116u. In some cases, the motion or motion intentions are defined by the user (e.g., user 101) or, in some embodiments, by a second user that has the capacity and/or authorization to input information into the biometric enabled virtual reality system 100, to be stored in memory 104m. This allows a caregiver, provider, physician, or otherwise authorized person(s) to monitor, create, or define the biometric signal data as generated by the user (e.g., user 101).

Figure 3:
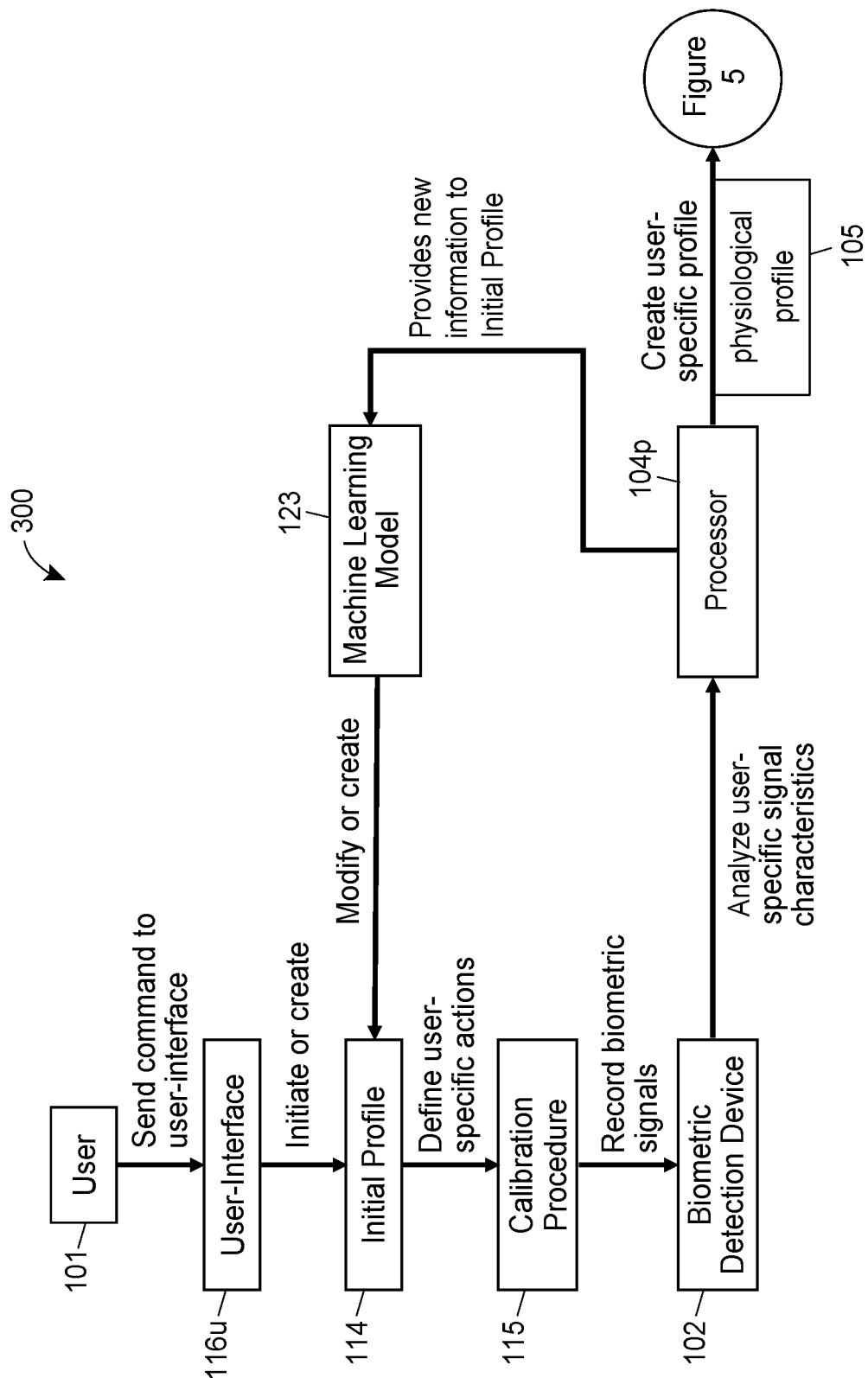
FIG. 3 is a block diagram illustrating an example method of creating a physiological profile of the user based on the biometric signal data of the user, in accordance with various embodiments herein, including, with example the methods of FIG. 4 and FIG. 5.

FIG. 3 is a block diagram illustrating an example biometric enabled virtual reality method 300 of creating a physiological profile (e.g., physiological profile 105) of a user (e.g., a user-specific profile of user 101) based on the biometric signal data of the user, in accordance with various embodiments herein. That is, biometric enabled virtual reality method 300 comprises creating, by computing instructions implementing an algorithm of method 300 and as illustrated by blocks of FIG. 3, a physiological profile 105 based on the analysis of the biometric signal data 103. In various embodiments the physiological profile 105 may be stored in memory 104m. Method 300 may be used to generate the physiological profile for use by the systems and methods described herein, including as described for FIGS. 4 and/or 5. In various embodiments, a processor (e.g., processor 104p) is communicatively coupled to a biometric detection device (e.g., biometric device 102) and is configured to create the physiological profile of the user (e.g., user 101) based on the biometric signal data (e.g., biometric signals and/or data 103, 110, and/or 110i) of the user.

In various embodiments, method 300 initiation, generation, and/or modification of a physiological profile (e.g., physiological profile 105) of a user by an adaptive learning component (e.g., a machine learning model 123), configured to identify user's 101 specific intentions to activate one or more muscles (e.g., as determined or detected from biometric signals and/or data 110). The machine learning model 123 continuously analyzes biometric signal data (e.g., biometric signals and/or data 103, 110, and/or 110i) of the user and may update, generate (or regenerate) a user's initial profile 114 associated with the user. The initial profile 114 is used to generate a user-specific, physiological profile 105 of the user. Such updating, generating, or regenerating may occur as the user 101 continues to use a biometric enabled virtual reality system 100, such as biometric enabled virtual reality system 100 as described herein for FIG. 1A. Over time, additional data (e.g., biometric signals and/or data 103, 110, and/or 110i) may be collected and/or stored in the memory 104m. The data may be used to train (or retrain) machine learning model 123 to predict, classify, or otherwise determine muscle intention(s) of the user to identify when a user (e.g., user 101) activates one or more muscles (e.g., as determined or detected from biometric signals and/or data 110).

Machine learning model(s), such as machine learning model 123, may be created and trained based upon example (e.g., "training data",) inputs or data (which may be termed "features" and "labels") in order to make valid and reliable predictions or classifications for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships of the model may then be provided subsequent inputs in order for the model, executing on a computing device, or otherwise processor(s) (e.g., processor 104p), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the computing device, or otherwise processor(s), may be required to find its own structure in unlabeled example inputs, where, for example multiple training iterations are executed by the computing device, or otherwise processor(s) to train multiple generations of models until a satisfactory model, e.g., a model that provides sufficient prediction accuracy when given test level or production level data or inputs, is generated. The disclosures herein may use one or more of such supervised or unsupervised machine learning techniques.

For example, in FIG. 3 the machine learning model 123 may be loaded in memory 104m and may be trained with biometric signal data (e.g., biometric signals and/or data 103, 110, and/or 110*i*) as analyzed from the biometric signals collected by biometric detection device 102 and as collected from the user 101. Once trained, machine learning model 123 may then recognize the user-specific intention to activate one or more muscles (e.g., as determined or detected from biometric signals and/or data 110), which may be based on analysis of muscle intention 112. The machine learning model 123 may then receive further or new biometric signal data (e.g., new biometric signals and/or data 103, 110, and/or 110*i*), wherein the biometric signals from the user 101 may be detected as a given user-specific and/or user-selected motion, which may then be associated with the analysis of muscle intention 112, to more accurately identify the user-specific intention to activate one or more muscles (e.g., as determined or detected from biometric signals and/or data 110).

Figure 5:
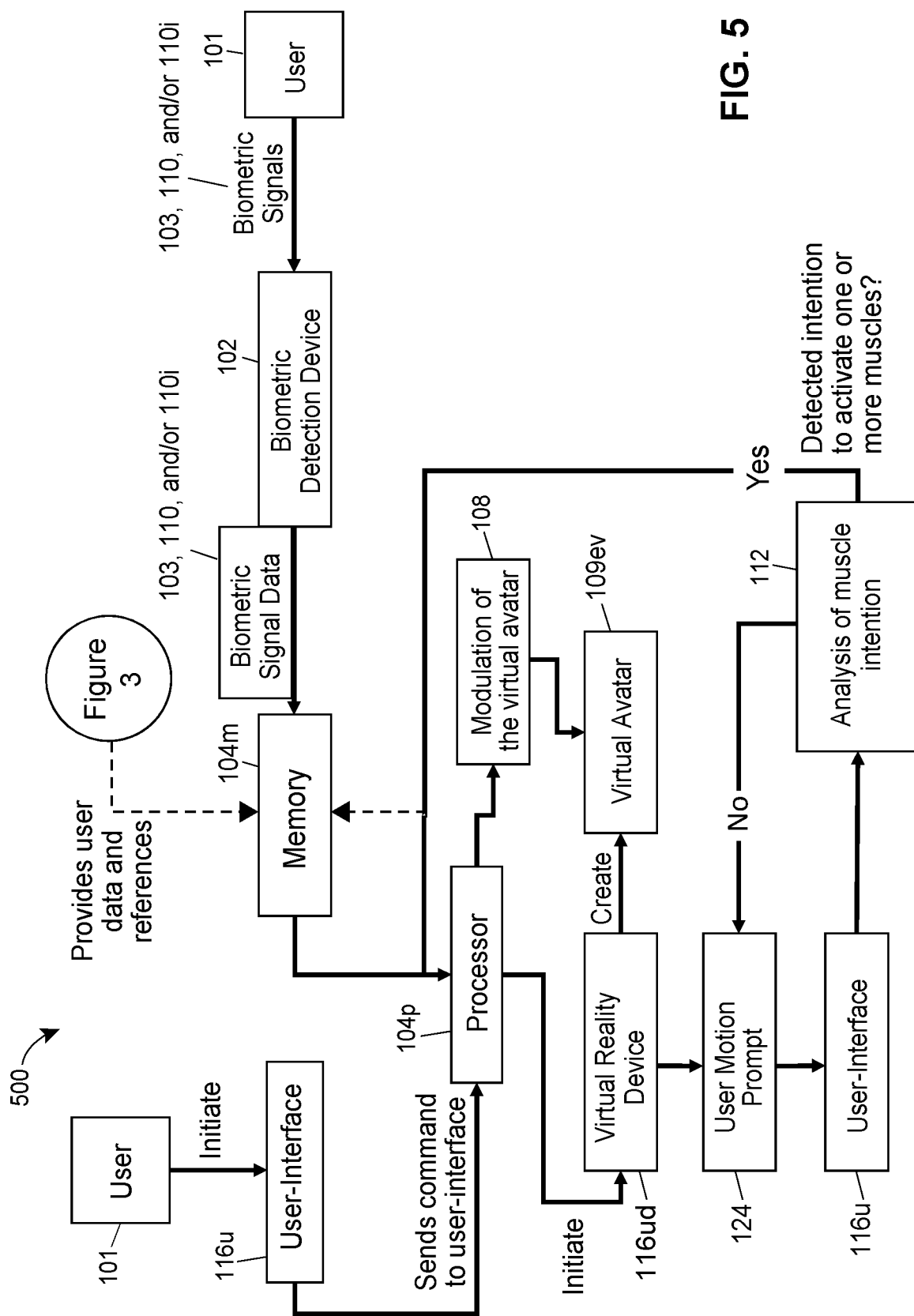
FIG. 5 is a block diagram illustrating an example biometric enabled virtual reality method for detecting one or more user intentions and manipulating virtual avatar control based on the one or more user intentions for providing kinematic awareness in holographic, two-dimensional (2D), or three-dimensional (3D) virtual space, in accordance with various embodiments herein.

In some embodiments, machine learning model 123 may be retrained or updated based on new biometric signal data (e.g., new biometric signals and/or data 103, 110, and/or 110*i*) of the user in order to optimize the machine learning model 123 for the identification or detection of user-specific intentions to activate one or more muscles (e.g., as determined or detected from biometric signals and/or data 110) and/or to improve the quality of the analysis of muscle intentions 112, which is further described herein for FIG. 5.

It is to be understood that FIG. 3 represents an example of using a machine-learning model to generate or modify a user's physiological profile, and that additional or different techniques (e.g., non-machine learning based techniques, such as procedural code or programmed logic) may be used to generate or modify a user's physiological profile.

In reference to FIG. 3, the execution of the algorithm of method 300 by processor 104*p* causes the processor 104*p* to bind biometric signal data (e.g., biometric signals and/or data 103, 110, and/or 110*i*) to initial profile 114 of user 101. The binding (e.g., storage or collection) of the biometric signal data can improve the efficacy of the binding should the biometric signal data demonstrate the intention to activate one or more muscles (e.g., as determined or detected from biometric signals and/or data 110), especially in subsequent temporal events wherein the same intention to activate one or more muscles (e.g., as determined or detected from biometric signals and/or data 110) occurs.

In some embodiments, biometric software component (e.g., stored in memory 104*m* and comprising computing instructions) may comprise a user-interface (e.g., a user-interface 116*u*) configured to receive one or more selections of the user 101 for customizing operation of biometric enabled virtual reality system 100. User-interface 116*u* may comprise various kinds or types, especially in relation to the user's specific needs. For example, in some embodiments, user-interface 116*u* may comprise a button user interface (not shown), such as a depressible and/or toggle button or switch, that when pressed causes the biometric enabled virtual reality system 100 to operate in different modes and/or states (e.g., calibration mode, activity mode, virtual reality mode, mobile mode, etc.). For example, the learning mode may be toggled or selected when the user trains the biometric enabled virtual reality system's 100 machine learning model 123 to more effectively detect, record, and/or recognize when the user's 101 biometric signal data (e.g., biometric signals and/or data 103, 110, and/or 110*i*) demonstrate the intention to activate one or more muscles (e.g., as determined or detected from biometric signals and/or data 110) subsequent to, or in accordance with, the analysis of muscle intention 112 as described herein.

Additionally, or alternatively, a user interface (e.g., user interface 116*u*) may comprise a virtual user interface (e.g., a visual interface) configured to display at least a portion of the initial profile 114. Such virtual user interface may comprise a graphic user interface (GUI). Additionally, or alternatively, the GUI may demonstrate the virtual visual field of the user 116*fv* in virtual reality, and/or on an external screen. Furthermore, the virtual user interface may comprise (a) a customized software command editing function, (b) a calibration or training button, and/or (c) a biometric detection device apparatus manager. For example, the customized software command editing function may be rendered via a GUI or screen of the biometric enabled virtual reality system 100 (e.g., on a wearable device such as an arm band, watch, mobile device screen, virtual reality headset, projector, or augmented reality headset). This customized software command editing function may allow a user (e.g., user 101) to edit parameters and/or configurations of the biometric detection device 102, the user interface device 116*ud*, or other aspects of the biometric enabled virtual reality system 100 for effecting or increasing performance and fidelity of biometric enabled virtual reality system 100. This may include editing the types, numbers, or characteristics of predetermined motions available by the biometric enabled virtual reality system 100 or that are stored in the memory 104*m*. Additionally, or alternatively, this may include user input (e.g., from user 101) to select, create, or otherwise modulate the current availability of predetermine motions that the biometric enabled virtual reality system 100 will use to prompt a user.

A calibration procedure 115 may be configured, e.g., by the user, to include new, modulated, or alternative motions to a list of predetermined motions that are stored in the memory 104*m*. In subsequent usage, when the user (e.g., user 101) is utilizing the system 100, the previously added new, modulated, or alternative motions (e.g., as stored in memory 104*m*) may be used for analysis of muscle intention 112 to determine the intention of the user to activate one or more muscles (e.g., as determined or detected from biometric signals and/or data 110). Calibration procedure 115 may allow a user to set up, train, or otherwise configure the biometric enabled virtual reality system 100. In some embodiments, this intention, as determined from calibration procedure 115, can then be represented in the virtual avatar 109*ev* to demonstrate the virtual representation of an intended motion (e.g., virtual avatar modulation 108).

As a still further example, an apparatus manager GUI of the biometric enabled virtual reality system 100 may be rendered via a GUI, screen, projector, or in virtual reality via a VR headset or display screen. The user (e.g., user 101) may access the apparatus manager GUI to adjust the sensitivity of the biometric detection device 102 (e.g., to detect the degree or fidelity to which biometric signals are detected), to read and analyze biometric signal data, to visualize live biometric signals, the update or change user profile 114, to filter biometric signal data, to alter physiological profile 105 settings stored in memory 104*m*, and/or adjust parameters that control the type(s) of control mechanisms used by biometric detection device 102.

In other embodiments, biometric detection device 102 may be tailored to the anatomy of the user 101 to generate a completely unique configuration for the user. The biometric enabled virtual reality system 100 may be further configured to allow for unique arrangements of the biometric detection device 102 by training the machine learning model 123 to optimize an analysis of muscle intention 112 of the user as detected through the biometric signals of the user 101. In similar embodiments, the user interface 116*u* allows the user 101 to enable certain aspects of the system 100 to allow for optimized biometric control and the detection of biometric signals. For example, optimization may occur when the user 101 provides at least one of the following data points (e.g., stored in the memory 104*m*): (a) number of biometric sensors, (b) location of biometric sensors, (c) physiological profile information, and/or (d) calibration or biometric motion data.

The biometric enabled virtual reality system 100, in some embodiments, may be configured to output a virtual representation of an intended motion 108*vr*, as based on biometric signal data of the user. For example, once biometric signals have been detected by the biometric detection device 102, processor 104*p* performs an analysis of muscle intention 112 based on the biometric signals. If it is determined that the user 101 has intended to activate one or more muscles (e.g., as determined or detected from biometric signals and/or data 110), the biometric signal data in correspondence with the intention to activate one or more muscles (e.g., as determined or detected from biometric signals and/or data 110) may be stored in the memory 104*m* to build a data library for the user profile 114 and/or physiological profile 105. Once the muscle intention has been analyzed and the intention to activate one or more muscles (e.g., as determined or detected from biometric signals and/or data 110) has been linked to a specific motion, the virtual avatar 109*ev* may be modulated or controlled by the processor 104*p* to demonstrate the virtual representation of the intended motion 108*vr* via user interface 116*u*. The virtual representation of the intended motion 108*vr* may include one or more intentions to activate one or more muscles (e.g., as determined or detected from biometric signals and/or data 110), and can be described as a complex motion wherein the intended movement is activating muscles that articulate about one or more skeletal joints. In some embodiments, the virtual representation of the intended motion 108*yr* is present in the virtual visual field of the user 116*fy* within either holographic, virtual 2D, or virtual 3D space. For example, the virtual representation of the intended motion 108*yr* may be visible through a VR headset, mobile device, display screen, projector, or otherwise visual manifestation device, such as those described herein, to demonstrate a motion of the user 101 in kinematic awareness space about the user 101.

As an example, and with reference to FIGS. 1A and 3, biometric detection device 102 is in superficial contact 120 with user 101 about the upper arm (e.g., roughly around the location of the brachialis muscle). User 101 has had an amputation below the elbow (e.g., amputated extremity 109*e*), that is missing the corporeal components of the forearm and wrist. In a visual field of the user 116*f*, the user 101 can see in real or ordinary space (without user interface device 116*ud*) the amputated arm below the elbow. The user has kinematic awareness positioning of the elbow about the user 101. Through user interface 116*u*, the user 101 sees or experiences a virtual avatar 109*ev* superimposed, in virtual space, over a virtual representation of the amputated extremity 109*e*. The virtual space is a virtual field of view 116*fy* that corresponds to the user's visual field 116*f* in ordinary space. The virtual avatar 109*ev* superimposed, in virtual space, over a virtual representation of the amputated extremity demonstrates or displays to the user an entire, intact extremity as if it were not amputated. The user interface 116*u* and/or the virtual visual field of the user 116*fy* provides the user (e.g., user 101) with a user motion prompt 124 to contract the brachialis muscle. If the user 101 creates biometric signals, that subsequent to analysis for muscle intention 112, demonstrate the intention to activate one or more muscles (e.g., as determined or detected from biometric signals and/or data 110) in correspondence with the user's 101 initial profile 114 for biometric signal data denoting the contraction of the brachialis muscle, then processor 104*p* will render or modulate virtual avatar 109*ev* to demonstrate or represent a virtual representation of the intended motion 108*yr* on user interface 116*u*. In this case, the virtual visual field of the user 116*fy* would show user 101 the virtual arm contracting at the elbow with the corporeal components of the forearm and wrist intact. Based on the biometric signal data, the processor 104*p* may modulate the speed, intensity, type of contraction (e.g., isometric, eccentric, or concentric muscle contraction), direction of contraction, combination of one or more muscle contractions, duration of contraction, and/or location of the virtual avatar 109*ev* in the virtual visual field of the user 116*fv*. In the present example, the virtual representation of the intended motion 108*vr*, being superimposed over the amputated extremity of the user (e.g., user 101), would then demonstrate the contraction of the brachialis muscle in the virtual visual field of the user 116*fv* to imitate how the contraction would appear, and feel, kinematically to the user 101 in the virtual visual field of the user 116*fv* as if the user 101's extremity 109*e* were not amputated, thereby providing kinematic awareness in holographic, 2D, or 3D virtual space.

The above example may be further applied when user 101 generates any amount, frequency, or duration of biometric signals that can be gathered by the biometric detection device 102. In certain embodiments, one or more sensors of biometric detection device 102 may be present to collect biometric signals from multiple different locations about the user 101 (e.g., as described for FIGS. 2C), allowing the biometric enabled virtual reality system 100 to classify the intention to activate one or more muscles (e.g., as determined or detected from biometric signals and/or data 110) about one or more corporeal components, which can be further utilized by the processor 104*p* to create complex virtual representations of the intended motion 108*vr*, or represent different motions that are overlapping temporally. For example, the system 100 could create a virtual representation of the intended motion 108*vr* of the user 101 to contract the deltoid, causing shoulder flexion, and subsequently followed by the contraction of the brachialis muscle to create a virtual representation of the arm bending at the elbow while the entire arm is presented virtually and kinematically to the user (e.g., via user interface 116*u*) to be in a state of shoulder flexion. In the present example, the motion can be further enhanced if the user 101 also intends to perform pronation or supination of the forearm, along with flexion of the wrist and/or fingers, especially at the same time of brachialis muscle contraction. It is to be noted that the biometric enabled virtual reality system 100 is not limited by the location or contraction of a specific group of muscles, and the above example is to demonstrate the system's 100 capabilities of categorizing and analyzing the biometric signals of the user 101 to create a virtual representation of an intended motion 108*vr* that may be complex in the amount of muscles activated (and the amount and/or type of biometric signals and/or data collected and used by system 100) over a particular temporal segment.

Figure 6:
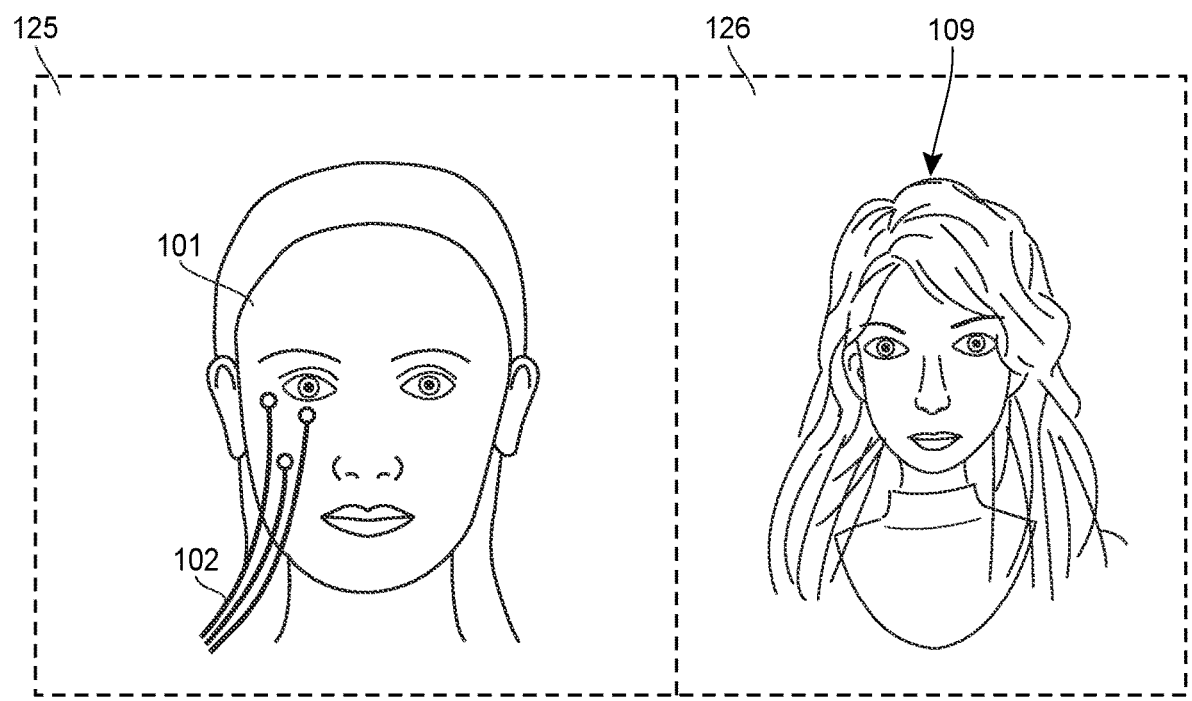
FIG. 6 illustrates a user, in ordinary space, utilizing biometric enabled virtual reality systems and methods, as described herein, to create a virtual avatar of herself, in virtual space and/or holographic space, based on the biometric signals of the user collected by a biometric detection device, in accordance with various embodiments herein.

When the user 101 has either initiated the calibration procedure 115 or is in active use of user interface device 116*ud* through the user interface 116*u*, the user interface 116*u* may provide the user (e.g., user 101) with a user motion prompt 124 (e.g., as described for FIG. 6). The user motion prompt 124 may have the user 101 perform an action within virtual space (e.g., such as to reach down and pick up an object, supinate the hand, contract the brachialis, etc.). Upon the user 101 performing the motion that was intended by the user motion prompt 124, the intention to activate one or more muscles (e.g., as determined or detected from biometric signals and/or data 110) may cause the processor 104p to create a virtual representation of the intended motion 108vr in correspondence with the user motion prompt 124. Should the analysis of the muscle intention 112 determine that the correct motion was conducted by the user, in some embodiments, the processor 104p may determine to store the associated biometric signals and/or data in the memory 104m in correspondence with the motion indicated by the user motion prompt 124. In subsequent prompts, wherein the biometric enabled virtual reality system 100 prompts the user to do a motion that has already been conducted, the previously stored biometric signal data in the memory 104m may be used as empirical data to more accurately determine the characteristics of the intention to activate one or more muscles (e.g., as determined or detected from biometric signals and/or data 110) on behalf of the user 101, especially during the analysis of muscle intention 112.

Virtual Avatar Creation

The following description describes example benefits and advantages of a biometrically controlled virtual reality system that allows a user to create and/or modulate a virtual avatar without a video capturing component.

In many of the preferred embodiments, the virtual avatar as represented in virtual space maintains relative temporal positioning to the user in ordinary space to resemble in-time movements. The user's actions are mimicked based on the positioning of the sensors of the biometric detection device 102 as described for FIGS. 1B and 10. In particular, the position of the sensors of the biometric device can collect and/or record signals of particular body parts, at specific locations on the user's body, each of which can provide a map or sensor map of different signals that processor 104p and/or machine learning model 123 can use to detect specific signals and/or actions. In these embodiments, the temporal aspect of mimicry is configured to represent the user's intentions to activate one or more muscles at the moment of intention provides the user with more control over the biometric system along with the prior art, as described herein.

Figure 7:
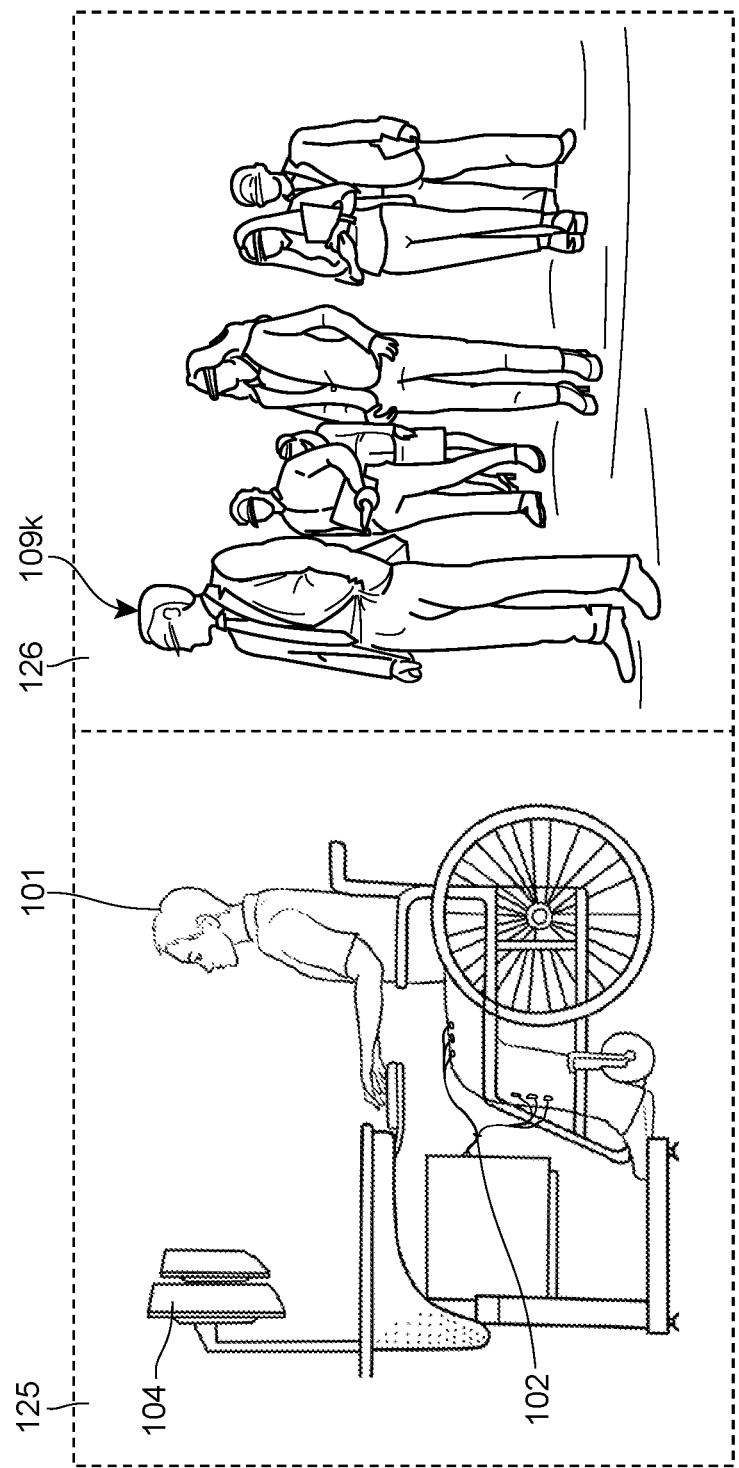
FIG. 7 illustrates an example embodiment comprising a wheelchair user with a biometric detection device attached to his leg in ordinary space with an example representation of the user's corresponding virtual avatar implemented in virtual space and/or holographic space, where the biometric enabled virtual reality systems and methods, as described herein, are configured to control an ambulatory avatar in the virtual space.

For example, a user (e.g., in some embodiments, user 101) is a wheelchair user, as described for FIG. 7, and would like to modulate their virtual avatar within a virtual chat room of their choice. Within this virtual chat room, the user, along with the other attending members, are depicted as cartoon humanoids that may walk, chat, or otherwise move within a virtual open space. The user, being a wheelchair user, traditionally would only be able to have themselves naturally depicted as a wheelchair user within the virtual space. However, with the biometric enabled virtual reality system, the user may choose to modulate their avatar to appear ambulatory and upright, as if not in a wheelchair.

In accordance with the above example, the user couples the biometric detection device (e.g., biometric detection device 102) with one or more muscles that the user may use to later indicate a motion. In this example, the indicated motion may correspond to moving one or more legs in a forward direction within the virtual space. Thus, as the user generates muscle intentions that correspond to moving one or more legs in a forward direction, the virtual avatar will demonstrate the same motions as indicated within virtual space.

In continuance with the above example, especially with a wheelchair user, the biometric detection device may be configured to collect biometric signal information directly from the user's legs. In the event that the user is capable of generating an intention to activate one or more of their leg muscles, the biometric detection device can then be configured to coordinate these intentions with the modulation of the virtual avatar—allowing the user to activate their lower extremity muscles to modulate the virtual avatar even in the event that the wheelchair user is not able to manifest a muscle movement.

In some embodiments, the biometric detection device is configured to detect signals from a different part of the user's body than what the system will output as a virtual avatar modulation event. For example, a wheelchair user has one atrophied leg and one amputated leg. The biometric detection device may be customized to collect biometric signal data from the atrophied leg, corresponding to the ipsilateral leg in the virtual avatar representation, whereas the rest of the biometric detection device is configured to collect biometric signal data from the user's abdomen, corresponding to the amputated leg in the virtual avatar representation, thus, providing the user with control over multiple extremities in virtual space, or holographic space, irrespective of them having the ability to initiate an intention to activate one or more muscles in only a single extremity.

In further embodiments as described herein, the biometric detection device may be configured to collect biometric signals in relation to a user's motion, pain, and/or accelerometric information to determine the movement of a user in space.

In many preferred embodiments, the user is capable of training the virtual reality enabled system (e.g., training machine learning model 123) to couple one or more series of biometric signal data (e.g., biometric signal data corresponding to quadricep flexion) to virtual reality movement of one or more virtual avatar representations (e.g., quadricep flexion of the virtual avatar representation). In many of these embodiments, the activation of one or more muscle groups may correlate instead with a general command for the virtual avatar, with non-limiting examples such as "walk forward", "stand", "handshake", "smile", etc.

In an embodiment, the system is configured to overlay, and/or replace, the user's associated third-party camera capture output with the resultant virtual avatar and the associated representations thereof as provided by the collection of biometric signal data. In these embodiments, the system may replace what would have traditionally been a camera-image output with the virtual avatar as generated by the system based on the biometric signal data of the user, and without the use of a camera.

Figure 4:
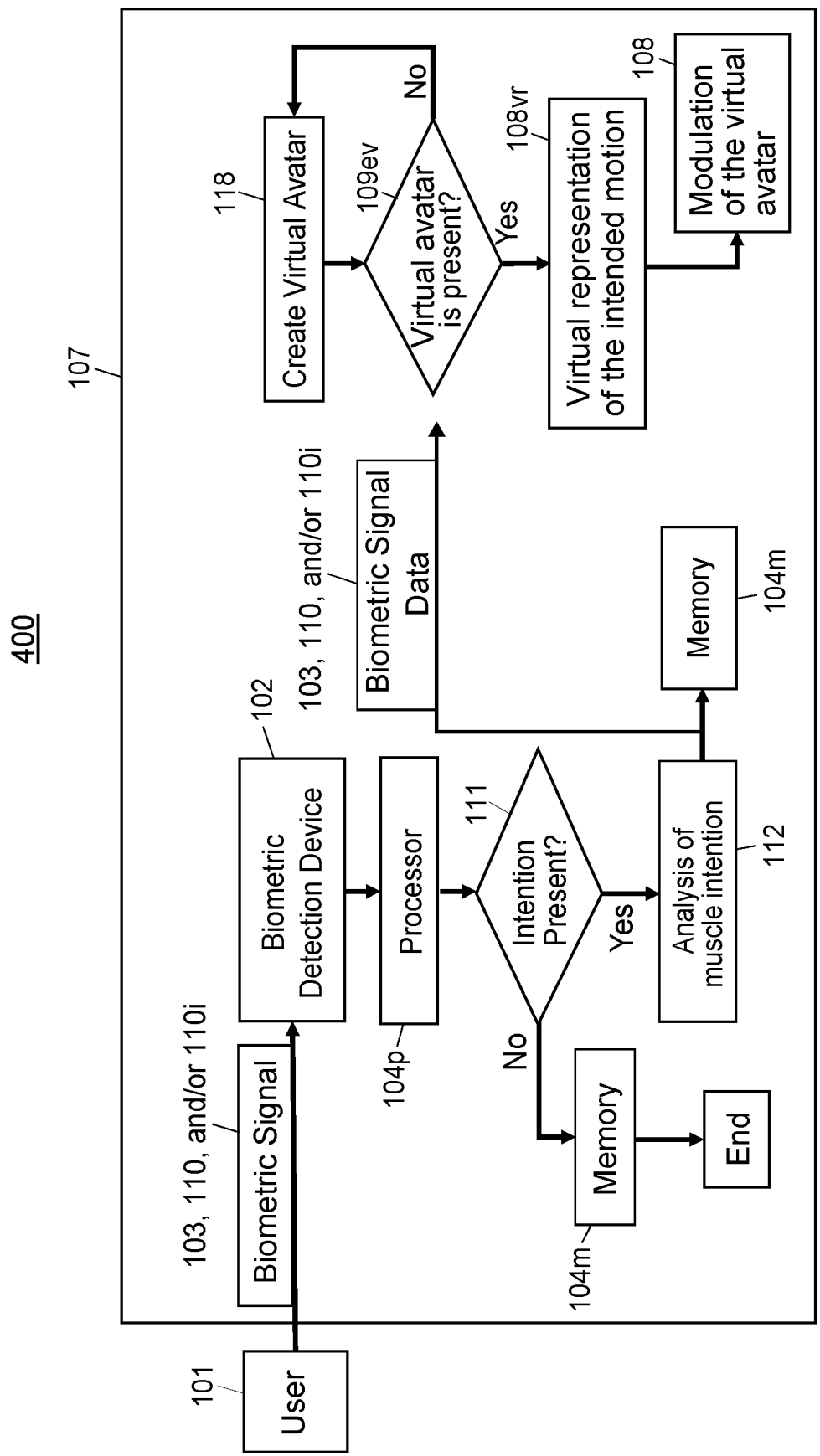
FIG. 4 is a block diagram illustrating an example biometric enabled virtual reality method for detecting one or more user intentions and modulating virtual avatar control based on the one or more user intentions for creation of one or more virtual avatars or objects in holographic, two-dimensional (2D), or three-dimensional (3D) virtual space, in accordance with various embodiments herein.

FIG. 4 is a block diagram illustrating an example biometric enabled virtual reality method 400 for detecting one or more user intentions and modulating virtual avatar control based on the one or more user intentions for creation of one or more virtual avatars or objects in holographic, 2D, or 3D virtual space, in accordance with various embodiments herein. Method 400 represents an algorithm or computing instructions that may be stored on a memory (e.g., memory 104m) and that is expectable by a processor (e.g., processor 104m). More generally, method 400 illustrates a creation and modulation protocol for a virtual avatar in accordance with the various embodiments described herein. Biometric enabled virtual reality method 400 provides accurate control of an avatar in a virtual reality space, e.g., through a user interface. Method 400 may be implemented by biometric enabled virtual reality system 100 describe herein.

Biometric enabled virtual reality method 400 comprises determining, based on analysis of a biometric signal data of a user, a virtual representation of an intended motion of the user corresponding to an intention of muscle activation of the user, the biometric signal data collected by a biometric detection device. In various aspects, determining the virtual representation of an intended motion of the user may comprise creating the virtual representation of an intended motion of the user for placement of a virtual avatar and/or object in virtual space or holographic space (e.g., in virtual 2D or 3D space). This is generally described for the various blocks (e.g., user 101 and analysis of muscle intention 112) of FIG. 4. For example, biometric signals (e.g., biometric signals and/or data 103, 110, and/or 110*i*, whether filtered or non-filtered) as illustrated by FIG. 4 may comprise biometric signal data 103 as detected biometric signals from the user (e.g., user 101). Such signals may be captured, collected, detected, or otherwise sensed by biometric detection device 102. Biometric detection device 102 may comprise various sensors, electrodes, leads, or the like for collecting the biometric signals from the user, where such sensors, electrodes, leads, etc., may comprise, for example, at least of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, or (j) one or more scleral search coils.

In various embodiments, a user-specific intention of user 101 to activate one or more muscles, or biometric signals or biometric signal data 103 thereof, may comprise at least one of: eccentric contraction of one or more muscles or muscle groups of a user (e.g., user 101); concentric muscle contraction of one or more muscles or muscle groups of a user (e.g., user 101); and/or isometric contraction of one or more muscles or muscle groups of the user (e.g., user 101). Such activity (e.g., any one or more types of contraction of a muscle and/or muscle groups) may cause electromyographic (EMG) signals to be produced by the user (e.g., user 101) in the form of biometric signals, being made available for the biometric detection device 102 to detect. Furthermore, such activity (e.g., any one or more types of contraction of a muscle and/or muscle groups) may cause additional biometric signals to become produced by the user (e.g., user 101), including but not limited to accelerometric, ultrasonic, optic, electric, temporal, thermal, and/or fluidic cues for detection by the biometric detection device 102.

At block 111, the biometric signal data 103 may be received by and/or processed by processor 104 to determine whether a specific muscle intention is present. If no such intention is present, then the biometric signal data 103 may be stored in memory 104*m* for later processing (e.g., for training machine learning model 123).

If a muscle intention is present, then processor 104*p* may begin an analysis of muscle intentions 112. For example, analysis of muscle intentions 112 comprise processor 104*p* determining or detecting whether specific signals (e.g., biometric data 110 as described for FIGS. 2A-2C) are present. An intention of muscle activation of a user (e.g., user 101) may comprise one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs. For intention of muscle activations that involve activation of neurons, such neurons may comprise of at least one of; (a) motor neurons, (b) neurons innervating one or more muscles; (c) interneurons, (d) sensory neurons, and/or (e) nociceptors.

Such analysis of muscle intentions 112 may be stored in memory 104*m* for current or later processing (e.g., for use of or for training of machine learning model 123).

Biometric enabled virtual reality method 400 further comprises modulating, based on the virtual representation of the intended motion and by a biometric software component comprising computational instructions configured for execution by a processor, virtual avatar control or output. This is generally described for items 108, 108*yr*, 109*ev*, and 118 of FIG. 4. In particular, in the embodiment of FIG. 4, analysis of muscle intentions 112 cause processor 104*p* to analyze biometric signal data for modulation of a virtual avatar 109*ev*. In various embodiments, modulation may comprise control, output, and/or creation of a virtual avatar or object (e.g., an object manipulated by the user in 2D or 3D virtual space). For example, in embodiments or stages where a virtual avatar 109*ev*, such as a graphic, VR graphic, or other image representing the user's extremity 109*e* has not yet generated, biometric enabled virtual reality method 400 creates (118) the virtual avatar 109*ev*.

For example, biometric enabled virtual reality method 400 comprises creating (118), based on the virtual avatar control or output, at least one of a virtual avatar representing one or more aspects of the user (e.g., extremity 109*e*) or an object manipulated by the user in holographic, virtual 2D space, or a virtual 3D space. Virtual avatar control or output comprises processor 104*p* creating or modifying a virtual avatar (e.g., virtual avatar 109*ev*) and/or controlling the virtual avatar 109*ev* in holographic, 2D, or 3D virtual space based on biometric data 103 of the user. A virtual avatar (e.g., virtual avatar 109*ev*) may comprise at least one of: (a) an avatar portion of a muscle group or an anatomy of the user, or (b) an avatar rendered in holographic, 2D virtual space, or 3D virtual space depicting the user corporeally different than the user appears in ordinary space. In addition, creating the virtual avatar comprises categorizing or classifying one or more types of user intended motions corresponding to the biometric signal data of the user. Still further, a virtual avatar is created or configured for rendering or controlling in holographic virtual 2D space, or the virtual 3D space. In particular, creating (118) virtual avatar 109*ev* comprises generating graphics or images based on the biometric signal data, where, for example, the various sensors, as attached to user 101, provide data to processor 104*p* such that processor, based on biometric signal data, and the positions of the sensors of biometric detection device 102 (e.g., as described for FIGS. 1B and 10), is able to map, in holographic, 2D, or 3D virtual space, a position of the user's extremity 109*e*. From the mapping, processor 104*p* may generate, and superimpose on extremity 109*e*, virtual avatar 109*ev* as viewable in holographic, 2D, or 3D virtual space via user interface 116*u* in the virtual visual field 116*fy* of the user. In particular, processor 104*p* may then provide a virtual representation of the intended motion 108*yr* of the virtual avatar in holographic, 2D, or 3D virtual space. In various embodiments, the virtual avatar may be configured for display on a virtual interface (e.g., user interface 116*u*) such that the virtual avatar is rendered on the virtual interface as part of a picture, a motion picture, a video, a video game, or one or more image frames.

In various embodiments, biometric enabled virtual reality method 400 comprises creating (118) a virtual avatar or the object in holographic, virtual 2D space, or the virtual 3D space based on at least one of: (1) the biometric signal data of a user (e.g., biometric data 103), and (2) user-specific specifications as provided by the user. The user-specific specifications may be provided by the user as described herein for FIG. 3. For example, the user-specific specifications may include at least one of: visual characteristics of the virtual avatar, or auditory characteristics of the virtual avatar, and wherein the user-specific specifications are selectable by the user from a predetermined list. Processor 104*p* may be configured to create a physiological profile (as described for FIG. 3) of the user based on the biometric signal data of the user, where the physiological profile includes the user-specific specifications.

Once created, or otherwise determined, additional virtual avatar modulation 108 of virtual avatar 109*ev* may occur in holographic, 2D, or 3D virtual space. For example, such modulation of a virtual avatar 109*ev* may comprise at least one of: (a) changing a color of the virtual avatar; (b) changing one or more dimensions of or distorting the virtual avatar; (c) translating the virtual avatar; (d) rotating the virtual avatar; (e) reflecting the virtual avatar about a predetermined axis; or (f) performing dilation on the virtual avatar.

In additional embodiments, virtual avatar modulation 108 of a virtual avatar (e.g., virtual avatar 109*ev*) may involve rendering of virtual avatar 109*ev* on user interface 116 for a variety of purposes and/or contexts. For example, a virtual avatar (e.g., virtual avatar 109*ev*) may be rendered via a virtual interface (e.g., user interface 116*u*) as representing at least one of the intention of muscle activation of the user or a motion of the user. In some embodiments, the virtual interface (e.g., user interface 116*u*) may be configured to be accessed or controlled by one or more additional authorized persons. In such embodiments, the virtual interface is configured to provide the additional authorized persons with one or more of: (a) display of the biometric signal data of the user or profile records, or; (b) input to provide the user with cues, notifications, questionnaires, and/or messages through the virtual interface.

In some embodiments, a virtual avatar may comprise an avatar or object depicted with one or more graphical features selected by a user (e.g., user 101). The one or more graphical features may be rendered as part of the virtual avatar in the 2D virtual space or 3D virtual space.

Kinematic Awareness and Phantom Limb Pain Treatment

The disclosure further describes use of biometric or biosignal detection devices (e.g., biometric detection device 102), and related biometric enabled virtual reality systems and methods, that utilizes a user's intention to move an extremity (e.g., extremity 109*e*) to augment a virtual avatar (e.g., virtual avatar 109*ev*) without the need of a visual cue or reference. Through the usage of advanced biometric detectors, the systems and methods disclosed herein measure a user's (e.g., user 101) intention to contract a muscle; specifically, through the measurement of biosignals (e.g., biometric data 103, 110, and/or 110*i*) that indicate a physiological intention for a muscle group to contract.

For example, every tissue in the body is electrically active. When a user attempts to initiate a movement, the associated muscles generates electromyographic (EMG) electrical signals with characteristics corresponding to the number of muscle fibers, the intensity of the movement, and duration for which the intended muscles are to contract. Such signals are described herein, for example, for FIGS. 1A-C and 2A-BC. By measuring such signals, or with signals similar to these, the systems and methods disclosed herein uses machine learning and pattern recognition algorithms (e.g., machine learning model 123) to identify the user's intention to activate a specific muscle group—even if the intention is not strong enough, or the user is unable, to provide movement. This aspect becomes increasingly relevant for users that require physical rehabilitation or require kinematic awareness cues to treat an ailment or condition.

In accordance with the disclosure herein, the number of muscle fibers that are recruited to perform an action as intended by the user are largely influenced by the number of motor neurons innervating said muscle fibers. In many embodiments, a number of muscle fibers that are attempting to be recruited to perform a user intention (e.g., flexing a muscle) may be correlated with the perceived effort on behalf of the user to perform said user intention. Furthermore, the location of muscle fibers that are recruited to perform a user intention, based on the specific configuration of the biometric detection device, may allow the system to determine which muscle fibers are being recruited to perform a muscle contraction, especially in correspondence to particular muscles and/or muscle groups. In these embodiments, the system may use the location of recruited motor neurons, neurons, and/or muscle fibers (as determined by a proximity or location of sensors, for example, as described for FIGS. 2A-2C herein) to determine the intended motion of the user. Subsequent to the identification of the user's intention to activate one or more muscles, and the identification of said muscles, the system, as initiated by the processor, may determine the intended motion on behalf of the user.

In an example in accordance with the disclosure herein, a biometric detection device (e.g., biometric detection device 102) may receive biometric signal data from the user that corresponds with the brachioradialis muscle. In such examples, the biometric enabled virtual reality system 100, as described herein, may determine that the user is attempting to perform elbow flexion, indicating to a processor (e.g., processor 104*p*) to modulate a virtual arm to perform elbow flexion in accordance with the collected biometric signal data, regardless if the user is able to perform elbow flexion in ordinary space. In the same example, if the biometric detection device receives information that many motor neurons are attempting to recruit muscle fibers, the resulting virtual avatar may represent a more forceful or stronger level of elbow flexion; this aspect becomes especially relevant when determining the amount of intended output strength as initiated by the user. In the same example still, if the biometric detection device receives information relating to fewer motor neurons innervating muscle fibers being recruited, that the user is attempting to perform an isometric contraction—as if to hold an object in virtual space. The above example is intended to be explanatory, and should not be construed as limiting in any fashion.

In the case of a user having an amputation, sometimes the user will experience pain associated with the body part that was amputated—even though there is no physical limb to represent it. This is a phenomenon referred to as Phantom Limb Pain (PLP). Although a component of the body may be amputated, in certain users, the nerves that would typically innervate an extremity may still be intact with the muscles in which they are coupled. Thus, a patient's phantom limb pain could be treated through "tricking" the brain that the body component is still, in fact, intact. This is done through the user contracting the muscles that correspond to the amputated body component while providing the brain with a kinematic awareness cue of the body component as if it were intact (e.g., a visual representation of the amputated limb). Traditionally, this kinematic awareness cue of the body component is created through recording the uninjured body component with a camera and recreating the image superimposed over the injured body component. The user would simultaneously move the uninjured body component while attempting to contract the injured component, creating a synchronous muscle contraction, visual cue, and activation of the innervating nerves—causing the brain to interpret the kinematic awareness cue as if the limb were not amputated, and in fact, performing movement the brain would expect through the corresponding muscle contraction. By providing the brain with a kinematic awareness cue of an amputated limb, research has demonstrated statistical significance in reducing the amount of phantom limb pain perceived by the user. The biometric enabled virtual reality systems and methods disclosed herein provide for measuring the intention of contracting a particular muscle group without using an uninjured body component as a visual reference via camera, mirror reflection, or similar visual recording technology.

In some embodiments and configurations as described herein, the user may have undergone rehabilitative surgery to improve their capacity to utilize one or more of their muscles (e.g., Targeted Muscle Reinnervation "TMR"), wherein a nerve or series of neurons are moved, reattached, or repurposed to innervate a target muscle. The target muscle may present as being different than the muscle the nerve or neurons were initially intended to innervate. In these embodiments and configurations, the biometric enabled virtual reality systems and methods disclosed herein may be configured to collect biometric signal data from the newly-innervated muscle and determine a user-specific movement in accordance with the location and purpose-function of the newly innervated muscle. It is to be understood by persons having ordinary skill in the art that such configurations are infinite in permutations, and the system's algorithms have been designed as such to allow for customizability and modularity to allow such vast quantities of permutations without sacrificing the user's capacity to biometrically control a virtual avatar.

The systems and methods disclosed herein do not require an uninjured body component as a reference to create a kinematic awareness cue to superimpose over the injured body component. Instead, the systems and methods disclosed herein uses biometric detectors to measure the body component's physiological signals to detect the intention for a muscle contraction directly. Thus, if a patient has a bilateral amputation, the systems and methods disclosed herein can be used on one, or both extremities, to create independent superimposed images of the body components, thus allowing the kinematic awareness cues to be controlled separately. Furthermore, more in-depth analytics such as contraction magnitude, limb orientation, complex movement identification, and gestures can be discerned through the biometric signals that are collected from the patient's injured body component. These biometric signals may then be used by the biometric enabled virtual reality systems and methods disclosed herein to create a virtual avatar of the injured body component, and through virtual space, project the avatar over where the user's body component would traditionally be; thus, creating a kinematic awareness cue of the injured body component without the need of a reference extremity. The avatar in virtual space may be embodied as a representation of the user's extremity, a representation of the biometric signals collected from the biometric detection device, an object to be controlled or manipulated, or simply a display of the user's intent to activate a muscle group.

For example, a user that has bilateral upper extremity amputations at the wrist would have the capability of creating a kinematic awareness cue in virtual reality through the intention (e.g., intentions 109*i*) to contract muscles that would normally correspond to the forearm, wrist, or components of the hand. By measuring the biometric signals through forearm muscles that correspond to the hand, the virtual reality system creates the kinematic awareness cue without a reference image as captured by a camera or reflected by a mirror. By comparison, traditional methods of creating a visual image of phantom limb movement would be impossible for this particular user because they do not have an uninjured limb that could provide itself as a visual reference. Furthermore, because the signals generated from the user are specific to that user, the biometric enabled virtual reality systems and methods disclosed herein may use artificial intelligence (e.g., machine learning model 123), including but not limited to deep learning capabilities and/or pattern recognition to create a biometric user profile that more accurately represents the different states of muscle contraction intention from a user. This allows the biometric enabled virtual reality systems and methods disclosed herein to improve upon the accuracy and precision in which identification a user's contraction of a muscle, the duration for which the intention to contract a muscle persists, and to the amplitude of which each is occurring. Through this functionality the systems and methods disclosed herein is able to present itself as a more versatile, accurate, and comprehensive technology in addressing users with unique complications while providing more accurate methods of demonstrating a virtual avatar, kinematic awareness cue, or superimposed image over an injured body component.

In many of the preferred embodiments, the user may have bilateral extremity amputations—prohibiting one limb functioning as a reference limb. In these scenarios, the system's functionality to measure the biometric signals from both of the amputated extremities allows the user to control one or more virtual avatars, each corresponding to the biometric signals detected from the corresponding amputated extremity, without the need for either a camera or referencing device.

The biometric enabled virtual reality systems and methods disclosed herein also address a need for an enhanced virtual reality treatment of neurological disorders that may be unique to a patient. Based on the machine learning aspect of the system (e.g., via machine learning model 123), the systems and methods disclosed herein may be used by a clinician, caregiver, or through self-use to rehabilitate, train, or otherwise assist in the neurological rehabilitation of one or more body components that may present with abnormal neurological control. The rehabilitation, training, or otherwise assisting in the neurological control may be used to improve the quality of life for a patient that has experienced a neurological deviation from a healthy norm due to an injury, amputation, genetic disorder, pathology, or otherwise degenerated nature of the user's nervous control capabilities of their injured body component.

FIG. 5 is a block diagram illustrating an example biometric enabled virtual reality method 500 for detecting one or more user intentions and manipulating virtual avatar control based on the one or more user intentions for providing kinematic awareness in holographic, two-dimensional (2D), or three-dimensional (3D) virtual space, in accordance with various embodiments herein. Method 500 represents an algorithm or computing instructions that may be stored on a memory (e.g., memory 104*m*) and that is expectable by a processor (e.g., processor 104*m*). Method 500 may be implemented by biometric enabled virtual reality system 100 describe herein. More generally, FIG. 5 illustrates how biometric enabled virtual reality system 100 modulates a virtual avatar (e.g., virtual avatar 109ev). FIG. 5 also demonstrates how different sources of information, such as detected biometric signals or data (e.g., biometric data 103) by biometric detection device 102, data of a physiological profile 105, and/or other empirical data sources can be used (e.g., by the processor 104p) to accurately modulate the virtual avatar (e.g., virtual avatar 109ev).

In various embodiments, biometric enabled virtual reality method 500 comprises determining, based on analysis of a biometric signal data of a user (e.g., 101), a virtual representation of an intended motion (e.g., virtual representation of the intended motion 108yr) of the user corresponding to an intention of muscle activation of the user. The virtual representation of the intended motion 108yr of the user corresponding to the intention of the muscle activation of the user may represent an intention to activate one or more muscles. The biometric signal data (e.g., biometric data 103) may be collected by a biometric detection device (e.g., biometric detection device 102), and stored in memory 104m. Biometric detection device 102 may comprise at least one of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, and/or (j) one or more scleral search coils.

Determination of a virtual representation of an intended motion of the user corresponding to an intention of muscle activation of the user may be performed as described herein with respect to FIGS. 3 and 4. For example, the one or more user intentions may comprise specific muscle activations such as a user intention to perform one or more gestures. As specific examples, an intention of muscle activation of the user may comprise one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs. Neurons indicative of intentions of muscle activation may comprise of at least one of; (a) motor neurons, (b) neurons innervating one or more muscles; (c) interneurons, (d) sensory neurons, or (e) nociceptors.

In addition, a physiological profile 105 may also be loaded into memory 104m and provided to processor 104p for user-specific modulation (e.g., virtual avatar modulation 108) of user 101. The physiological profile of the user may be created based on the biometric signal data of the user and/or user-specific information (such as information/answers provided by the user via the virtual interface).

Biometric enabled virtual reality method 500 further comprises modulating (e.g., virtual avatar modulation 108), based on the virtual representation of the intended motion and by a biometric software component comprising computational instructions (e.g., represented by the algorithm of method 500) executed by a processor (e.g., processor 104p), virtual avatar control or output. Modulating, based on the virtual representation of the intended motion and by a biometric software component comprising computational instructions executed by a processor, virtual avatar control or output may be performed as described herein with respect to FIGS. 3 and 4.

In the example of FIG. 5, user 101 controls a virtual reality device (e.g., user interface device 116ud) which may create or render virtual avatar 109ev. Virtual avatar 109ev may comprise at least one of: (a) an avatar portion of a muscle group or an anatomy of the user, or (b) an avatar portion of an amputated portion of the user's body rendered as a virtual body part of the user as non-amputated. In various embodiments, the virtual avatar may rendered on a virtual interface (e.g., user interface device 116ud) as part of a picture, a motion picture, a video, a video game, or one or more image frames.

In some embodiments, virtual reality device (e.g., user interface device 116ud) renders a user motion prompt 124 to prompt the user to contract a muscle, make a certain gesture, or otherwise perform an action to generate biometric data 103. For example, a virtual interface (e.g., user interface device 116ud) is configured to prompt the user to perform a gesture intention that corresponds to the intention of muscle activation. For example, in some embodiments, method 500 may comprise determining a pain threshold of the user. The virtual interface may be rendered including a prompt instructing the user position or move a body portion of the user to attenuate the pain threshold or optimize a treatment of the body portion or corresponding body portion of the user. In some embodiments, the virtual avatar may rendered via the virtual interface as representing at least one of the intention of muscle activation of the user or a motion of the user. This may provide a similar effect to the user looking into a mirror, or may, at least, provide relief to the user regarding phantom limb pain.

In some embodiments, the virtual interface (e.g., user interface 116u) is configured to be accessed or controlled by one or more additional authorized persons. In accordance with such embodiments, the user 101 may receive user motion prompts 124 to indicate an intention to activate one or more muscles (e.g., as determined or detected from biometric signals and/or data 110) on behalf of a user 101. For example, the virtual interface is configured to provide the additional authorized persons with one or more of: (a) display of the biometric signal data of the user or profile records, or; (b) input to provide the user with cues, notifications, questionnaires, or messages through the virtual interface. Authorized persons may be able to access the virtual interface on behalf of the user. In various embodiments, the user may be paralyzed or has reduced neurological control over an injured extremity. Additionally, or alternatively, the user may be unable to perform the intended motion in ordinary space.

The user may further interact with user interface 116u for providing additional input or information (e.g., for generation of physiological profile 105). Biometric information or user information may then be used by processor 104p to perform an analysis of muscle intentions 112 of the user 101. If the one or more muscle intentions are not detected, a user may be prompted 124 again to perform an action to generate biometric data 103. However, if one or more muscle intentions are detected, then processor 104p may begin or continue virtual avatar modulation 108 of virtual avatar 109ev.

Virtual avatar modulation 108 of virtual avatar 109ev, via biometric enabled virtual reality method 500, may comprise manipulating, based on the virtual avatar control or output, a virtual avatar (e.g., virtual avatar 109ev) representing one or more aspects of at least one of the user or an object manipulated by the user in holographic space, virtual 2D space, or virtual 3D space. The virtual avatar may represent or depict one or more aspects of at least one of the user or the object manipulated by the user correspond to at least one of: the biometric signal data of the user, or; (b) a data stream representation of the biometric signal data of the user. Manipulating the virtual avatar may comprise categorizing or classifying one or more types of user intended motions corresponding to the biometric signal data of the user.

In various embodiments, the virtual avatar (e.g., virtual avatar 109ev) is rendered by a virtual interface (e.g., user interface device 116ud) configured to provide the user a kinematic awareness in the virtual 2D space or the virtual 3D space. For example, the virtual avatar control or output is configured to provide as at least one of: attenuation of a pain condition or as a kinematic awareness rehabilitative cue for muscular neurological control of the user.

In some embodiments, the pain condition of the user is treated through virtual administration of a kinematic awareness cue. The kinematic awareness rehabilitative cue provides a non-opioid pain management alternative. Such kinematic awareness rehabilitative cue may also be applicable to user conditions of pain such as brachial plexopathy, stroke, or for a user with Complex Regional Pain Syndrome (CPRS). The kinematic awareness rehabilitative cue can be provided to treat phantom limb pain where the user is an amputee. For example, manipulating and rendering of the virtual avatar (e.g., virtual avatar 109ev) on the virtual interface (e.g., user interface 116u) causes the user to experience a decreased perception of phantom pain. More generally, a kinematic awareness rehabilitative cue is provided by method for muscular neurological control of the user and comprises a temporally representative visual cue, as rendered in holographic space, virtual 2D space, or the virtual 3D space on user interface 116u, that corresponds to a virtual position of an amputated or non-present limb (e.g. virtual avatar 109ev) of the user in reference to the user based on the biometric data (e.g., biometric data 103) of the user. In some embodiments, a quantity value of pain of the user may be determined, where the quantity value may be calculated, by processor 104p, through at least one of: (a) analysis of the biometric signal data indicating the pain of the user, or, (b) input, via the virtual interface (e.g., user interface 116u), of user-specific responses or pain-related information as provided by the user.

Method 500 demonstrates a flow diagram or of an example virtual avatar 109ev control algorithm in accordance with the various embodiments herein. The biometric enabled virtual reality system 100 provides real time (or near-real time), analyzed movements based on the biometric signal data as detected by the biometric device 102. In various embodiments, software components may be stored in the memory 104m and/or otherwise configured or set up as described in FIG. 5 or elsewhere herein. In various embodiments, biometric detection device 102 may receive a raw signal data, or otherwise biometric signals from a user 101 and generate, transform, pass through, identify, and/or otherwise detect biometric signal data for analysis by a processor 104p. Biometric detection device 102 may detect raw signal data or otherwise biometric signals of user 101 as described herein.

As described for FIG. 5, user 101 may be provided with a user motion prompt 124 to initiate modulation of virtual avatar 109ev. For example, a user 101 acts upon the user interface 116u to initiate the processor 104p, enabling system 100 to receive input data and to output a virtual experience via VR device 116ud. The VR device may prompt 124 user 101 to perform a specific or series of muscle movements. In some embodiments, the user motion prompt 124 is delivered to the user 101 through a GUI of the user interface 116u, and in other embodiments, is delivered to the user through the virtual visual field of the user 116fv, or combination thereof. Once the motion prompt 124 has been delivered to the user 101, the processor 104p utilizes the biometric signal data 103 to perform an analysis of the muscle intention 112 to determine whether the user 101 performed the same intention to activate one or more muscles (e.g., as determined or detected from biometric signals and/or data 103, 110, and/or 110i) that corresponds with the user motion prompt 124. In the event that the user 101 performed the motion intended by the user motion prompt 124, the processor 104p uses the biometric signal data from the corresponding intention to activate one or more muscles (e.g., as determined or detected from biometric signals and/or data 103, 110, and/or 110i) to drive the characteristic modulation of the virtual avatar 109ev in holographic space, 2D space, or 3D space. In some embodiments, the modulation of the virtual avatar 108 involves using characteristics of the biometric signal data 103, 110, and/or 110i to determine the extent to which the virtual avatar 109ev is modulated. For example, if the user 101 provides weak biometric signals, in correspondence with the user motion prompt 124, then a proportionally weak modulation of the virtual avatar 108 occurs, in part, or in full, as determined by the processor 104p, and vice-versa for strong signals, and/or other signals ranging there between.

In various embodiments the biometric signal data 103 may be analyzed with at least one of the following algorithms or computational techniques, including: (a) fuzzy logic; (b) pattern classification; (c) computational neural networks; (d) forward dynamic modeling; or (e) support vector machines. In various embodiments, such data analysis may comprise creating at least one user-specific physiological profile 105 as described herein. The user-specific physiological profile is unique to the user, and may be used in computational software components to increase the accuracy and precision of the identification of the intention to activate one or more muscles (e.g., as determined or detected from biometric signals and/or data 110).

In many of the disclosed embodiments, and with reference to the examples of FIGS. 3, 4, and 5, a user (e.g., user 101) may utilize the biometric enabled virtual reality system 100 for the control and modulation of a virtual avatar 109ev for social purposes. In these embodiments, the user 101 will utilize the biometric detection device 102 to drive the modulation of a virtual avatar 108, the virtual avatar 108ev being displayed in virtual space 126. In many of these embodiments, space 126 represents holographic space within the virtual visual field of the user 116fv for the user 101 or other person(s) within the social program or system. In these embodiments further, the modulation of the virtual avatar 109ev is controlled by the processor 104p, receiving the biometric signals from the biometric detection device 102, and using the biometric signal data 112 to modulate the virtual avatar 109ev.

In many preferred embodiments, the user 101 has the option to change, modify, or otherwise alter the characteristics of a virtual avatar 109h to better suit their personal or social needs. For example, FIG. 6 illustrates a user 101, in ordinary space 125, utilizing biometric enabled virtual reality systems and methods, as described herein, to create a virtual avatar 109h of herself, in virtual space 126 based on the biometric signals collected by a biometric detection device 102, in accordance with various embodiments herein. In similar embodiments, the user 101 in ordinary space 125 may use the system 100 as described to create a virtual avatar 109h in virtual space 126, wherein User 101 may determine that her virtual avatar 109h should have brown hair, green eyes, or other characteristics of the virtual avatar 109h that the user 101 chooses. In many of these embodiments, the biometric enabled virtual reality system 100 will provide the opportunity to modify the virtual avatar 109h through the user interface 116u, providing user 101 with the ability to demonstrate themselves in virtual space 126 as a virtual avatar 109h with modular characteristics. In many of these embodiments, the user 101 is provided with the capacity to demonstrate themselves in virtual space 126 wherein the space further represents a holographic space.

In another example, a stroke patient (not shown) may have lost a substantial amount of control over one side of their face, having only unilateral control over the nerves and muscles. Through the usage of the systems and methods disclosed herein, the stroke patient would be capable of depicting themselves in virtual space (e.g., a ZOOM or GOOGLE HANGOUTS conference) as if they maintained bilateral control of their facial muscles and nerves. These utility and advantages become increasingly apparent in the description of the technology as provided herein.

In accordance with the above embodiment, the user's 101 modulation of the characteristics of the virtual avatar 109h merely changes the appearance of the avatar in their chosen virtual space 126, wherein the virtual space 126 may be holographic space, but does not necessarily determine the relative functionality of the virtual avatar 109h within the user's 101 chosen medium of virtual space 126. In these cases, wherein the user 101 has decided to modulate the characteristics of the virtual avatar 109h, the user 101 may still be able to control and modulate the virtual avatar 109h through the biometric detection device 102, as determined by the processor 104p, when initiating the intention to activate one or more muscles (e.g., as determined or detected from biometric signals and/or data 103, 110, and/or 110i). Based on the configuration and setup of the initial profile 114, the system 100 may serve user-unique purposes regarding the signal characteristics of the biometric signal data 112 and which aspects of the virtual avatar 109h are to be modified, based on the analysis of the biometric signal data 103, 110, and/or 110i.

In some embodiments, the virtual 2D space or the virtual 3D space in which a virtual avatar (e.g., virtual avatar 109h) is rendered, may be provided by a third-party platform such that a virtual avatar (e.g., virtual avatar 109h) is configured for rendering or controlling in the holographic space, virtual 2D space, or the virtual 3D space of the third-party platform. A third-party platform may comprise a social chat room, meeting space, conference, or like program that enables the user to display their virtual avatar to themselves and/or other persons in virtual space.

FIG. 7 illustrates an example embodiment comprising a wheelchair user 101 with a biometric detection device 102 attached to his leg in ordinary space 125 with an example representation of the user's corresponding virtual avatar 109k implemented in virtual space 126, where the biometric enabled virtual reality systems and methods, as described herein, are configured to control the virtual avatar 109k as an ambulatory avatar in the virtual space 126. Control of virtual avatar 109k provided by biometric enabled virtual reality system 100 as described for FIGS. 3-5 herein, including as described for control and/or modulation a virtual avatar 109ev. In the embodiment of FIG. 7, user 101 depicts himself in virtual space 126 differently he appears in ordinary space 125, the virtual space 126 further comprise a holographic image being displayed in holographic space. For example, user 101 is a wheelchair user and does not have the physical capacity to stand, walk, or otherwise ambulate in ordinary space 125, but nonetheless desires to appear as ambulatory in virtual space 126, wherein the virtual space 126 may further comprise a virtual avatar 109k in holographic. User 101 selects, via user interface 116u, the characteristics of their virtual avatar 109k as an ambulatory virtual avatar. User 101 may further select a configuration for his biometric detection device 102 that may initiate the intention to activate one or more muscles (e.g., as determined or detected from biometric signals and/or data 103, 110, and/or 110i) that correspond with the action to have their virtual avatar 109k ambulate in virtual space 126.

In the example of FIG. 7, wheelchair user 101 may be attending a virtual hangout meeting with his coworkers and friends, wherein each of the attendees are depicted as animated figures in a hangout room to freely walk about and converse with one another. The wheelchair user 101 may determine that he would not like to be depicted in virtual space as being constantly sitting, especially when the other users are ambulatory. In this scenario, the wheelchair user may be able to depict themselves in virtual space as if they were not wheelchair bound, and through the usage of a biometric detection device and biometric enabled virtual reality system 100 as described herein, ambulate around the virtual hangout space as if they were not a wheelchair user. The modulation of their virtual avatar 109k, as depicted in virtual space, becomes a modular and virtual avatar that is based off of the biometric signals collected from the biometric detection device 102. The virtual avatar 109k, being an extension of the user's biometric signals, comprises aspects that correspond to the biometric signal data of the wheelchair user (e.g., user 101) as collected and analyzed by processor 104p, and as modulated as describe herein.

ASPECTS OF THE DISCLOSURE

1. A biometric enabled virtual reality system configured to detect one or more user intentions and to manipulate virtual avatar control based on the one or more user intentions for providing kinematic awareness in holographic space, two-dimensional (2D) virtual space, or three-dimensional (3D) virtual space, the biometric enabled virtual reality system comprising: a biometric detection device configured to collect biometric signal data of a user, a processor communicatively coupled to the biometric detection device, and; a biometric software component comprising computational instructions configured for execution by the processor, the computational instructions, that when executed by the processor, cause the processor to: determine, based on analysis of the biometric signal data of the user, a virtual representation of an intended motion of the user corresponding to an intention of muscle activation of the user, and modulate, based on the virtual representation of the intended motion, virtual avatar control or output comprising: manipulating a virtual avatar representing one or more aspects of at least one of the user or an object manipulated by the user in holographic space, virtual 2D space, or a virtual 3D space, wherein the virtual avatar is rendered by a virtual interface configured to provide the user a kinematic awareness in the holographic space, virtual 2D space, or the virtual 3D space.

2. The biometric enabled virtual reality system of aspect 1, wherein the intention of muscle activation of the user comprises one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs.

3. The biometric enabled virtual reality system of aspect 2, wherein the neurons may comprise of at least one of; (a)

motor neurons, (b) neurons innervating one or more muscles; (c) interneurons, (d) sensory neurons, or (e) nociceptors.

4. The biometric enabled virtual reality system of any one or more of aspects 1-3, wherein the virtual interface prompts the user to perform a gesture intention that corresponds to the intention of muscle activation.

5. The biometric enabled virtual reality system of any one or more of aspects 1-4, wherein the virtual avatar comprises at least one of: (a) an avatar portion of a muscle group or an anatomy of the user, or (b) an avatar portion of an amputated portion of the user's body rendered as a virtual body part of the user as non-amputated.

6. The biometric enabled virtual reality system of any one or more of aspects 1-5, wherein the virtual avatar is rendered via the virtual interface as representing at least one of the intention of muscle activation of the user or a motion of the user.

7. The biometric enabled virtual reality system of any one or more of aspects 1-6, wherein the virtual avatar representing one or more aspects of at least one of the user or the object manipulated by the user correspond to at least one of: the biometric signal data of the user, or; (b) a data stream representation of the biometric signal data of the user.

8. The biometric enabled virtual reality system of any one or more of aspects 1-7, wherein the virtual avatar is rendered on the virtual interface as part of a picture, a motion picture, a video, a video game, or one or more image frames.

9. The biometric enabled virtual reality system of any one or more of aspects 1-8, wherein the biometric detection device comprises at least one of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, or (j) one or more scleral search coils.

10. The biometric enabled virtual reality system of any one or more of aspects 1-9, wherein manipulating the virtual avatar comprises categorizing or classifying one or more types of user intended motions corresponding to the biometric signal data of the user.

11. The biometric enabled virtual reality system of any one or more of aspects 1-10, wherein the virtual avatar control or output is configured to provide as at least one of: attenuation of a pain condition or as a kinematic awareness rehabilitative cue for muscular neurological control of the user.

12. The biometric enabled virtual reality system of aspect 11, wherein the pain condition of the user is treated through virtual administration of a kinematic awareness cue.

13. The biometric enabled virtual reality system of any one or more of aspects 1-12, wherein the manipulating and rendering of the virtual avatar on the virtual interface causes the user to experience a decreased perception of phantom pain.

14. The biometric enabled virtual reality system of any one or more of aspects 1-13, wherein a kinematic awareness rehabilitative cue for muscular neurological control of the user comprises a temporally representative visual cue, provided in the holographic space, virtual 2D space, or the virtual 3D space, that corresponds to a virtual position of an amputated or non-present limb of the user in reference to the user based on the biometric data of the user.

15. The biometric enabled virtual reality system of any one or more of aspects 1-14, wherein the biometric software component further comprises computational instructions, that when executed by the processor, cause the processor to: determine a quantity value of pain of the user, the quantity value calculated through at least one of: (a) analysis of the biometric signal data indicating the pain of the user, or, (b) input, via the virtual interface, of user-specific responses or pain-related information as provided by the user.

16. The biometric enabled virtual reality system of any one or more of aspects 1-15, wherein the virtual interface is configured to be accessed or controlled by one or more additional authorized persons, wherein the virtual interface is configured to provide the additional authorized persons with one or more of: (a) display of the biometric signal data of the user or profile records, or; (b) input to provide the user with cues, notifications, questionnaires, or messages through the virtual interface.

17. The biometric enabled virtual reality system of any one or more of aspects 1-16, wherein the virtual representation of the intended motion of the user corresponding to the intention of the muscle activation of the user represents an intention to activate one or more muscles.

18. The biometric enabled virtual reality system of aspect 17, wherein the user is paralyzed or has reduced neurological control over an injured extremity 19. The biometric enabled virtual reality system of aspect 17, wherein the user is unable to perform the intended motion in ordinary space.

20. The biometric enabled virtual reality system of any one or more of aspects 1-19, wherein the biometric software component comprises computational instructions that when executed by the processor, further cause the processor to: determine a pain threshold of the user; and render, on the virtual interface, a prompt instructing the user position or move a body portion of the user to attenuate the pain threshold or optimize a treatment of the body portion or corresponding body portion of the user.

21. The biometric enabled virtual reality system of any one or more of aspects 1-21, wherein the biometric software component comprises computational instructions that when executed by the processor, further cause the processor to: create a physiological profile of the user based on the biometric signal data of the user.

22. A biometric enabled virtual reality method for detecting one or more user intentions and manipulating virtual avatar control based on the one or more user intentions for providing kinematic awareness in holographic space, two-dimensional (2D) virtual space, or three-dimensional (3D) virtual space, the biometric enabled virtual reality method comprising: determining, based on analysis of a biometric signal data of a user, a virtual representation of an intended motion of the user corresponding to an intention of muscle activation of the user, the biometric signal data collected by a biometric detection device; modulating, based on the virtual representation of the intended motion and by a biometric software component comprising computational instructions executed by a processor, virtual avatar control or output; and manipulating, based on the virtual avatar control or output, a virtual avatar representing one or more aspects of at least one of the user or an object manipulated by the user in holographic space, a virtual 2D space, or a virtual 3D space, wherein the virtual avatar is rendered by a virtual interface configured to provide the user a kinematic awareness in holographic space, the virtual 2D space, or the virtual 3D space.

23. The biometric enabled virtual reality method of aspect 22, wherein the intention of muscle activation of the user comprises one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs.

24. The biometric enabled virtual reality method of aspect 23, wherein the neurons may comprise of at least one of: (a) motor neurons, (b) neurons innervating one or more muscles; (c) interneurons, (d) sensory neurons, or (e) nociceptors.

25. The biometric enabled virtual reality method of any one or more of aspects 22-24, wherein the virtual interface prompts the user to perform a gesture intention that corresponds to the intention of muscle activation.

26. The biometric enabled virtual reality method of any one or more of aspects 22-25, wherein the virtual avatar comprises at least one of: (a) an avatar portion of a muscle group or an anatomy of the user, or (b) an avatar portion of an amputated portion of the user's body rendered as a virtual body part of the user as non-amputated.

27. The biometric enabled virtual reality method of any one or more of aspects 22-26, wherein the virtual avatar is rendered via the virtual interface as representing at least one of the intention of muscle activation of the user or a motion of the user.

28. The biometric enabled virtual reality method of any one or more of aspects 22-27, wherein the virtual avatar representing one or more aspects of at least one of the user or the object manipulated by the user correspond to at least one of: the biometric signal data of the user, or; (b) a data stream representation of the biometric signal data of the user.

29. The biometric enabled virtual reality method of any one or more of aspects 22-28, wherein the virtual avatar is rendered on the virtual interface as part of a picture, a motion picture, a video, a video game, or one or more image frames.

30. The biometric enabled virtual reality method of any one or more of aspects 22-29, wherein the biometric detection device comprises at least one of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, or (j) one or more scleral search coils.

31. The biometric enabled virtual reality method of any one or more of aspects 22-30, wherein manipulating the virtual avatar comprises categorizing or classifying one or more types of user intended motions corresponding to the biometric signal data of the user.

32. The biometric enabled virtual reality method of any one or more of aspects 22-31, wherein the virtual avatar control or output is configured to provide as at least one of: attenuation of a pain condition or as a kinematic awareness rehabilitative cue for muscular neurological control of the user.

33. The biometric enabled virtual reality method of aspect 32, wherein the pain condition of the user is treated through virtual administration of a kinematic awareness cue.

34. The biometric enabled virtual reality method of any one or more of aspects 22-33, wherein the manipulating and rendering of the virtual avatar on the virtual interface causes the user to experience a decreased perception of phantom pain.

35. The biometric enabled virtual reality method of any one or more of aspects 22-34, wherein a kinematic awareness rehabilitative cue for muscular neurological control of the user comprises a temporally representative visual cue, in holographic space, the virtual 2D space, or the virtual 3D space, that corresponds to a virtual position of an amputated or non-present limb of the user in reference to the user based on the biometric data of the user.

36. The biometric enabled virtual reality method of any one or more of aspects 22-35 further comprising determining a quantity value of pain of the user, the quantity value calculated through at least one of: (a) analysis of the biometric signal data indicating the pain of the user, or, (b) input, via the virtual interface, of user-specific responses or pain-related information as provided by the user.

37. The biometric enabled virtual reality method of any one or more of aspects 22-36, wherein the virtual interface is configured to be accessed or controlled by one or more additional authorized persons, wherein the virtual interface is configured to provide the additional authorized persons with one or more of: (a) display of the biometric signal data of the user or profile records, or; (b) input to provide the user with cues, notifications, questionnaires, or messages through the virtual interface.

38. The biometric enabled virtual reality method of any one or more of aspects 22-37, wherein the virtual representation of the intended motion of the user corresponding to the intention of the muscle activation of the user represents an intention to activate one or more muscles.

39. The biometric enabled virtual reality method of aspect 38, wherein the user is paralyzed or has reduced neurological control over an injured extremity 40. The biometric enabled virtual reality method of aspect 38, wherein the user is unable to perform the intended motion in ordinary space.

41. The biometric enabled virtual reality method of any one or more of aspects 22-40 further comprising determining a pain threshold of the user; and render, on the virtual interface, a prompt instructing the user position or move a body portion of the user to attenuate the pain threshold or optimize a treatment of the body portion or corresponding body portion of the user.

42. The biometric enabled virtual reality method of any one or more of aspects 22-41 further comprising creating a physiological profile of the user based on the biometric signal data of the user.

43. A tangible, non-transitory computer-readable medium storing instructions for or detecting one or more user intentions and manipulating virtual avatar control based on the one or more user intentions for providing kinematic awareness in holographic space, two-dimensional (2D), or three-dimensional (3D) virtual space, that when executed by one or more processors cause the one or more processors to: determine, based on analysis of a biometric signal data of a user, a virtual representation of an intended motion of the user corresponding to an intention of muscle activation of the user, the biometric signal data collected by a biometric detection device; modulate, based on the virtual representation of the intended motion and by a biometric software component comprising computational instructions executed by a processor, virtual avatar control or output; and manipulate, based on the virtual avatar control or output, a virtual avatar representing one or more aspects of at least one of the user or an object manipulated by the user in holographic space, virtual 2D space, or a virtual 3D space, wherein the virtual avatar is rendered by a virtual interface configured to provide the user a kinematic awareness in the holographic space, the virtual 2D space, or the virtual 3D space.

Additional Aspects of the Disclosure

1. A biometric enabled virtual reality system configured to detect one or more user intentions and to modulate virtual avatar control based on the one or more user intentions for creation of one or more virtual avatars or objects in holographic space, two-dimensional (2D) space, or three-dimensional (3D) virtual space, the biometric enabled virtual reality system comprising: a biometric detection device configured to collect biometric signal data of a user, a processor communicatively coupled to the biometric detection device, and; a biometric software component comprising computational instructions configured for execution by the processor, the computational instructions, that when executed by the processor, cause the processor to: determine, based on analysis of the biometric signal data of the user, a virtual representation of an intended motion of the user corresponding to an intention of muscle activation of the user, and modulate, based on the virtual representation of the intended motion, virtual avatar control or output comprising creating at least one of a virtual avatar representing one or more aspects of the user or an object manipulated by the user in holographic space, virtual 2D space, or a virtual 3D space, wherein the virtual avatar or object is created in the holographic space, virtual 2D space, or the virtual 3D space based on at least one of: (1) the biometric signal data of a user, or (2) user-specific specifications as provided by the user.

2. The biometric enabled virtual reality system of any one or more of aspect 1, wherein the intention of muscle activation of the user comprises one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs.

3. The biometric enabled virtual reality system of aspect 2, wherein the neurons may comprise of at least one of; (a) motor neurons, (b) neurons innervating one or more muscles; (c) interneurons, (d) sensory neurons, or (e) nociceptors.

4. The biometric enabled virtual reality system of any one or more of aspects 1-3, wherein the virtual avatar comprises at least one of: (a) an avatar portion of a muscle group or an anatomy of the user, or (b) an avatar rendered in the holographic space, the 2D virtual space, or 3D virtual space depicting the user corporeally different than the user appears in ordinary space.

5. The biometric enabled virtual reality system of any one or more of aspects 1-4, wherein the virtual avatar is rendered via a virtual interface as representing at least one of the intention of muscle activation of the user or a motion of the user.

6. The biometric enabled virtual reality system of aspect 5, wherein the virtual interface is configured to be accessed or controlled by one or more additional authorized persons, wherein the virtual interface is configured to provide the additional authorized persons with one or more of: (a) display of the biometric signal data of the user or profile records, or; (b) input to provide the user with cues, notifications, questionnaires, or messages through the virtual interface.

7. The biometric enabled virtual reality system of any one or more of aspects 1-6, wherein the virtual avatar comprises an avatar depicted with one or more graphical features selected by the user, wherein the one or more graphical features are rendered as part of the virtual avatar in the holographic space, 2D virtual space, or 3D virtual space.

8. The biometric enabled virtual reality system of any one or more of aspects 1-7, wherein the virtual avatar is configured for display on a virtual interface, and wherein the virtual avatar is rendered on the virtual interface as part of a picture, a motion picture, a video, a video game, or one or more image frames.

9. The biometric enabled virtual reality system of any one or more of aspects 1-8, wherein the biometric detection device comprises at least one of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, or (j) one or more scleral search coils.

10. The biometric enabled virtual reality system of any one or more of aspects 1-9, wherein creating the virtual avatar comprises categorizing or classifying one or more types of user intended motions corresponding to the biometric signal data of the user.

11. The biometric enabled virtual reality system of any one or more of aspects 1-10, wherein the virtual avatar is configured for rendering or controlling in the virtual 2D space or the virtual 3D space.

12. The biometric enabled virtual reality system of any one or more of aspects 1-11, wherein the holographic space, virtual 2D space, or the virtual 3D space is provided by a third-party platform, and wherein the virtual avatar is configured for rendering or controlling in the holographic space, virtual 2D space, or the virtual 3D space of the third-party platform.

13. The biometric enabled virtual reality system of any one or more of aspects 1-12, wherein the modulation of the virtual avatar further comprises at least one of: (a) changing a color of the virtual avatar; (b) changing one or more dimensions of or distorting the virtual avatar; (c) translating the virtual avatar; (d) rotating the virtual avatar; (e) reflecting the virtual avatar about a predetermined axis; or (f) performing dilation on the virtual avatar.

14. The biometric enabled virtual reality system of any one or more of aspects 1-13, wherein the user-specific specifications include at least one of: visual characteristics of the virtual avatar, or auditory characteristics of the virtual avatar, and wherein the user-specific specifications are selectable by the user from a predetermined list.

15. The biometric enabled virtual reality system of any one or more of aspects 1-14, wherein the biometric software component comprises computational instructions that when executed by the processor, further cause the processor to: create a physiological profile of the user based on the biometric signal data of the user, wherein the physiological profile comprises the user-specific specifications.

16. A biometric enabled virtual reality method for detecting one or more user intentions and modulating virtual avatar control based on the one or more user intentions for creation of one or more virtual avatars or objects in holographic space, two-dimensional (2D) virtual space, or three-dimensional (3D) virtual space, the biometric enabled virtual reality method comprising: determining, based on analysis of a biometric signal data of a user, a virtual representation of an intended motion of the user corresponding to an intention of muscle activation of the user, the biometric signal data collected by a biometric detection device; modulating, based on the virtual representation of the intended motion and by a biometric software component comprising computational instructions configured for execution by a processor, virtual avatar control or output; and creating, based on the virtual avatar control or output, at least one of a virtual avatar representing one or more aspects of the user or an object manipulated by the user in a holographic space, a virtual 2D space, or a virtual 3D space, wherein the avatar or the object is created in holographic space, the virtual 2D space, or the virtual 3D space based on at least one of: (1) the biometric signal data of a user, or (2) user-specific specifications as provided by the user.

17. The biometric enabled virtual reality method of aspect 16, wherein the intention of muscle activation of the user comprises one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs.

18. The biometric enabled virtual reality method of aspect 17, wherein the neurons may comprise of at least one of; (a) motor neurons, (b) neurons innervating one or more muscles; (c) interneurons, (d) sensory neurons, or (e) nociceptors.

19. The biometric enabled virtual reality method of any one or more of aspects 16-18, wherein the virtual avatar comprises at least one of: (a) an avatar portion of a muscle group or an anatomy of the user, or (b) an avatar rendered in the holographic space, the 2D virtual space, or 3D virtual space depicting the user corporeally different than the user appears in ordinary space.

20. The biometric enabled virtual reality method of any one or more of aspects 16-19, wherein the virtual avatar is rendered via a virtual interface as representing at least one of the intention of muscle activation of the user or a motion of the user.

21. The biometric enabled virtual reality method of aspect 20, wherein the virtual interface is configured to be accessed or controlled by one or more additional authorized persons, wherein the virtual interface is configured to provide the additional authorized persons with one or more of: (a) display of the biometric signal data of the user or profile records, or; (b) input to provide the user with cues, notifications, questionnaires, or messages through the virtual interface.

22. The biometric enabled virtual reality method of any one or more of aspects 16-21, wherein the virtual avatar comprises an avatar depicted with one or more graphical features selected by the user, wherein the one or more graphical features are rendered as part of the virtual avatar in the holographic space, 2D virtual space, or 3D virtual space.

23. The biometric enabled virtual reality method of any one or more of aspects 16-22, wherein the virtual avatar is configured for display on a virtual interface, and wherein the virtual avatar is rendered on the virtual interface as part of a picture, a motion picture, a video, a video game, or one or more image frames.

24. The biometric enabled virtual reality method of any one or more of aspects 16-23, wherein the biometric detection device comprises at least one of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, or (j) one or more scleral search coils.

25. The biometric enabled virtual reality method of any one or more of aspects 16-24, wherein creating the virtual avatar comprises categorizing or classifying one or more types of user intended motions corresponding to the biometric signal data of the user.

26. The biometric enabled virtual reality method of any one or more of aspects 16-25, wherein the virtual avatar is configured for rendering or controlling in the virtual 2D space or the virtual 3D space.

27. The biometric enabled virtual reality method of any one or more of aspects 16-26, wherein the holographic space, virtual 2D space, or the virtual 3D space is provided by a third-party platform, and wherein the virtual avatar is configured for rendering or controlling in the holographic space virtual 2D space, or the virtual 3D space of the third-party platform.

28. The biometric enabled virtual reality method of any one or more of aspects 16-27, wherein the modulation of the virtual avatar further comprises at least one of: (a) changing a color of the virtual avatar; (b) changing one or more dimensions of or distorting the virtual avatar; (c) translating the virtual avatar; (d) rotating the virtual avatar; (e) reflecting the virtual avatar about a predetermined axis; or (f) performing dilation on the virtual avatar.

29. The biometric enabled virtual reality method of any one or more of aspects 16-28, wherein the user-specific specifications include at least one of: visual characteristics of the virtual avatar, or auditory characteristics of the virtual avatar, and wherein the user-specific specifications are selectable by the user from a predetermined list.

30. The biometric enabled virtual reality method of any one or more of aspects 16-29 further comprising creating a physiological profile of the user based on the biometric signal data of the user, wherein the physiological profile comprises the user-specific specifications.

31. A tangible, non-transitory computer-readable medium storing instructions for detecting one or more user intentions and modulating virtual avatar control based on the one or more user intentions for creation of one or more virtual avatars or objects in holographic space, two-dimensional (2D), or three-dimensional (3D) virtual space, that when executed by one or more processors cause the one or more processors to: determine, based on analysis of a biometric signal data of a user, a virtual representation of an intended motion of the user corresponding to an intention of muscle activation of the user, the biometric signal data collected by a biometric detection device; modulate, based on the virtual representation of the intended motion and by a biometric software component comprising computational instructions configured for execution by a processor, virtual avatar control or output; and create, based on the virtual avatar control or output, at least one of a virtual avatar representing one or more aspects of the user or an object manipulated by the user in a holographic space, a virtual 2D space, or a virtual 3D space, wherein the avatar or the object is created in the holographic space, the virtual 2D space, or the virtual 3D space based on at least one of: (1) the biometric signal data of a user, or (2) user-specific specifications as provided by the user.

Additional Disclosure

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A biometric enabled virtual reality system configured to detect one or more user intentions and to modulate virtual avatar control based on the one or more user intentions for creation of one or more virtual avatars or objects in holographic space, two-dimensional (2D) virtual space, or three-dimensional (3D) virtual space, the biometric enabled virtual reality system comprising:
   a biometric detection device configured to collect biometric signal data of a user,
   a processor communicatively coupled to the biometric detection device, and;
   a biometric software component comprising computational instructions configured for execution by the processor, the computational instructions, that when executed by the processor, cause the processor to:
      determine, based on analysis of the biometric signal data of the user, a virtual representation of an intended motion of the user corresponding to an intention of muscle activation of the user, and
      modulate, based on the virtual representation of the intended motion, virtual avatar control or output comprising creating at least one of a virtual avatar representing one or more aspects of the user or an object manipulated by the user in a holographic space, a virtual 2D space, or a virtual 3D space,
   wherein the virtual avatar or object is created in the holographic space, the virtual 2D space, or the virtual 3D space based on at least one of: (1) the biometric signal data of a user, or (2) user-specific specifications as provided by the user,
   wherein the intention of muscle activation of the user comprises one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs.

2. The biometric enabled virtual reality system of claim 1, wherein the neurons may comprise of at least one of; (a) motor neurons, (b) neurons innervating one or more muscles; (c) interneurons, (d) sensory neurons, or (e) nociceptors.

3. The biometric enabled virtual reality system of claim 1, wherein the virtual avatar comprises at least one of: (a) an avatar portion of a muscle group or an anatomy of the user, or (b) an avatar rendered in the holographic space, the 2D virtual space, or 3D virtual space depicting the user corporeally different than the user appears in ordinary space.

4. The biometric enabled virtual reality system of claim 1, wherein the virtual avatar is rendered via a virtual interface as representing at least one of the intention of muscle activation of the user or a motion of the user.

5. The biometric enabled virtual reality system of claim 4, wherein the virtual interface is configured to be accessed or controlled by one or more additional authorized persons, wherein the virtual interface is configured to provide the additional authorized persons with one or more of: (a) display of the biometric signal data of the user or profile records, or; (b) input to provide the user with cues, notifications, questionnaires, or messages through the virtual interface.

6. The biometric enabled virtual reality system of claim 1, wherein the virtual avatar comprises an avatar depicted with one or more graphical features selected by the user, wherein the one or more graphical features are rendered as part of the virtual avatar in the holographic space, the 2D virtual space, or 3D virtual space.

7. The biometric enabled virtual reality system of claim 1, wherein the virtual avatar is configured for display on a virtual interface, and wherein the virtual avatar is rendered on the virtual interface as part of a picture, a motion picture, a video, a video game, or one or more image frames.

8. The biometric enabled virtual reality system of claim 1, wherein the biometric detection device comprises at least one of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, or (j) one or more scleral search coils.

9. The biometric enabled virtual reality system of claim 1, wherein creating the virtual avatar comprises categorizing or classifying one or more types of user intended motions corresponding to the biometric signal data of the user.

10. The biometric enabled virtual reality system of claim 1, wherein the virtual avatar is configured for rendering or controlling in the holographic space, virtual 2D space, or the virtual 3D space.

11. The biometric enabled virtual reality system of claim 1, wherein the holographic space, the virtual 2D space, or the virtual 3D space is provided by a third-party platform, and wherein the virtual avatar is configured for rendering or controlling in the holographic space, the virtual 2D space, or the virtual 3D space of the third-party platform.

12. The biometric enabled virtual reality system of claim 1, wherein the modulation of the virtual avatar further comprises at least one of: (a) changing a color of the virtual avatar; (b) changing one or more dimensions of or distorting the virtual avatar; (c) translating the virtual avatar; (d) rotating the virtual avatar; (e) reflecting the virtual avatar about a predetermined axis; or (f) performing dilation on the virtual avatar.

13. The biometric enabled virtual reality system of claim 1, wherein the user-specific specifications include at least one of: visual characteristics of the virtual avatar, or auditory characteristics of the virtual avatar, and wherein the user-specific specifications are selectable by the user from a predetermined list.

14. The biometric enabled virtual reality system of claim 1, wherein the biometric software component comprises computational instructions that when executed by the processor, further cause the processor to: create a physiological profile of the user based on the biometric signal data of the user, wherein the physiological profile comprises the user-specific specifications.

15. A biometric enabled virtual reality method for detecting one or more user intentions and modulating virtual avatar control based on the one or more user intentions for creation of one or more virtual avatars or objects in holographic space, two-dimensional (2D) virtual space, or three-dimensional (3D) virtual space, the biometric enabled virtual reality method comprising:
determining, based on analysis of a biometric signal data of a user, a virtual representation of an intended motion of the user corresponding to an intention of muscle activation of the user, the biometric signal data collected by a biometric detection device;
modulating, based on the virtual representation of the intended motion and by a biometric software component comprising computational instructions configured for execution by a processor, virtual avatar control or output; and
creating, based on the virtual avatar control or output, at least one of a virtual avatar representing one or more aspects of the user or an object manipulated by the user in a holographic space, virtual 2D space, or a virtual 3D space,
wherein the avatar or the object is created in the holographic space, the virtual 2D space, or the virtual 3D space based on at least one of: (1) the biometric signal data of a user, or (2) user-specific specifications as provided by the user, and
wherein the intention of muscle activation of the user comprises one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs.

16. The biometric enabled virtual reality method of claim 15, wherein the neurons may comprise of at least one of; (a) motor neurons, (b) neurons innervating one or more muscles; (c) interneurons, (d) sensory neurons, or (e) nociceptors.

17. The biometric enabled virtual reality method of claim 15, wherein the virtual avatar comprises at least one of: (a) an avatar portion of a muscle group or an anatomy of the user, or (b) an avatar rendered in the holographic space, the 2D virtual space, or 3D virtual space depicting the user corporeally different than the user appears in ordinary space.

18. The biometric enabled virtual reality method of claim 15, wherein the virtual avatar is rendered via a virtual interface as representing at least one of the intention of muscle activation of the user or a motion of the user.

19. The biometric enabled virtual reality method of claim 18, wherein the virtual interface is configured to be accessed or controlled by one or more additional authorized persons, wherein the virtual interface is configured to provide the additional authorized persons with one or more of: (a) display of the biometric signal data of the user or profile records, or; (b) input to provide the user with cues, notifications, questionnaires, or messages through the virtual interface.

20. The biometric enabled virtual reality method of claim 15, wherein the virtual avatar comprises an avatar depicted with one or more graphical features selected by the user, wherein the one or more graphical features are rendered as part of the virtual avatar in the holographic space, 2D virtual space, or 3D virtual space.

21. The biometric enabled virtual reality method of claim 15, wherein the virtual avatar is configured for display on a virtual interface, and wherein the virtual avatar is rendered on the virtual interface as part of a picture, a motion picture, a video, a video game, or one or more image frames.

22. The biometric enabled virtual reality method of claim 15, wherein the biometric detection device comprises at least one of: (a) one or more electromyographic electrodes, (b) one or more inertial measurement units, (c) one or more accelerometers, (d) one or more barometers; (e) one or more ultrasonic sensors, (f) one or more infrared sensors, (g) one or more pressure sensors, (h) one or more electroencephalogram electrodes, (i) one or more electrooculogram sensors, or (j) one or more scleral search coils.

23. The biometric enabled virtual reality method of claim 15, wherein creating the virtual avatar comprises categorizing or classifying one or more types of user intended motions corresponding to the biometric signal data of the user.

24. The biometric enabled virtual reality method of claim 15, wherein the virtual avatar is configured for rendering or controlling in the holographic space, the virtual 2D space, or the virtual 3D space.

25. The biometric enabled virtual reality method of claim 15, wherein the holographic space, the virtual 2D space, or the virtual 3D space is provided by a third-party platform, and wherein the virtual avatar is configured for rendering or controlling in the holographic space, the virtual 2D space, or the virtual 3D space of the third-party platform.

26. The biometric enabled virtual reality method of claim 15, wherein the modulation of the virtual avatar further comprises at least one of: (a) changing a color of the virtual avatar; (b) changing one or more dimensions of or distorting the virtual avatar; (c) translating the virtual avatar; (d) rotating the virtual avatar; (e) reflecting the virtual avatar about a predetermined axis; or (f) performing dilation on the virtual avatar.

27. The biometric enabled virtual reality method of claim 15, wherein the user-specific specifications include at least one of: visual characteristics of the virtual avatar, or auditory characteristics of the virtual avatar, and wherein the user-specific specifications are selectable by the user from a predetermined list.

28. The biometric enabled virtual reality method of claim 15 further comprising creating a physiological profile of the user based on the biometric signal data of the user, wherein the physiological profile comprises the user-specific specifications.

29. A tangible, non-transitory computer-readable medium storing instructions for detecting one or more user intentions and modulating virtual avatar control based on the one or more user intentions for creation of one or more virtual avatars or objects in holographic space, two-dimensional (2D) virtual space, or three-dimensional (3D) virtual space, that when executed by one or more processors cause the one or more processors to:
  determine, based on analysis of a biometric signal data of a user, a virtual representation of an intended motion of the user corresponding to an intention of muscle activation of the user, the biometric signal data collected by a biometric detection device;
  modulate, based on the virtual representation of the intended motion and by a biometric software component comprising computational instructions configured for execution by a processor, virtual avatar control or output; and
  create, based on the virtual avatar control or output, at least one of a virtual avatar representing one or more aspects of the user or an object manipulated by the user in a holographic space, virtual 2D space, or a virtual 3D space,
  wherein the avatar or the object is created in the holographic space, the virtual 2D space, or the virtual 3D space based on at least one of: (1) the biometric signal data of a user, or (2) user-specific specifications as provided by the user,
  wherein the intention of muscle activation of the user comprises one or more of: (a) a concentric muscle contraction, (b) an isometric muscle contraction, (c) an eccentric muscle contraction, or (d) an activation of neurons in a specific location on the user's body, the activation invoked by the user, intending to activate a muscle, regardless of whether or not muscle activation occurs.

* * * * *

UNITED STATES PATENT AND TRADEMARK OFFICE
CERTIFICATE OF CORRECTION

| | | |
|---|---|---|
| PATENT NO. | : 11,644,899 B2 | Page 1 of 1 |
| APPLICATION NO. | : 17/237337 | |
| DATED | : May 9, 2023 | |
| INVENTOR(S) | : Blair Andrew Lock et al. | |

It is certified that error appears in the above-identified patent and that said Letters Patent is hereby corrected as shown below:

In the Specification

At Column 1, Line number 12, please insert:
--Statement of U.S. Government Support
This invention was made with government support under W81XWH-20-1-0873 awarded by the Defense Health Agency, Medical Research and Development Branch. The government has certain rights in the invention.--

Signed and Sealed this
Twenty-eighth Day of October, 2025

John A. Squires
*Director of the United States Patent and Trademark Office*